United States Patent
Yoon

(10) Patent No.: US 10,184,067 B2
(45) Date of Patent: Jan. 22, 2019

(54) PAPER COATING MATERIAL HAVING ENVIRONMENT-FRIENDLY, WATER-PROOF AND OIL-PROOF PROPERTIES, AND METHOD OF MANUFACTURING THE SAME

(71) Applicant: REPAPER INC., Hwasung-si, Gyunggi-do (KR)

(72) Inventor: Cheol Yoon, Gyeonggi-do (KR)

(73) Assignee: REPAPER INC., Hwasung-si (KR)

( * ) Notice: Subject to any disclaimer, the term of this patent is extended or adjusted under 35 U.S.C. 154(b) by 0 days.

(21) Appl. No.: 15/716,968

(22) Filed: Sep. 27, 2017

(65) Prior Publication Data

US 2018/0094165 A1 Apr. 5, 2018

(30) Foreign Application Priority Data

Sep. 30, 2016 (KR) .......................... 10-2016-0126701

(51) Int. Cl.
| | |
|---|---|
| *C09D 183/04* | (2006.01) |
| *C09D 183/10* | (2006.01) |
| *C09D 5/02* | (2006.01) |
| *D21H 19/20* | (2006.01) |
| *D21H 27/10* | (2006.01) |
| *D21H 21/16* | (2006.01) |
| C07F 7/22 | (2006.01) |
| C08G 77/442 | (2006.01) |

(52) U.S. Cl.
CPC ............. *C09D 183/04* (2013.01); *C09D 5/02* (2013.01); *C09D 183/10* (2013.01); *D21H 19/20* (2013.01); *D21H 21/16* (2013.01); *D21H 27/10* (2013.01); *C07F 7/2224* (2013.01); *C08G 77/442* (2013.01)

(58) Field of Classification Search
CPC .................................................... C08G 77/442
See application file for complete search history.

(56) References Cited

FOREIGN PATENT DOCUMENTS

| | | | |
|---|---|---|---|
| JP | H06-306324 A | 11/1994 |
| JP | 2000-45199 A | 2/2000 |
| JP | 2013-155368 A | 8/2013 |
| KR | 10-2017-0111001 A | 10/2017 |

OTHER PUBLICATIONS

Abstract for KR 1752340 (Jun. 2017).*
Abstract for CN 105504622 (Apr. 2016).*
Korean Notice of Allowance dated Jun. 2, 2017 from KIPO in connection with the counterpart Korean Patent Application No. 10-2016-1026701 with a partial translation.

* cited by examiner

*Primary Examiner* — Marc S Zimmer
(74) *Attorney, Agent, or Firm* — Hauptman Ham, LLP

(57) ABSTRACT

Provided are a paper coating material having environment-friendly, water-proof, and oil-proof properties, and a method of manufacturing the same. The paper coating material includes a copolymer emulsion in which a silicon-based polymer and an acryl-based polymer are copolymerized, the copolymer emulsion having the weight average molecular weight of 100,000 to 200,000, and a colloidal aqueous solution of gelatinized polyvinyl alcohol to be mixed with the copolymer emulsion. The environment-friendly paper coated with the environment-friendly coating material according to the present invention is excellent in water-proof, oil-proof and heat sealing properties, harmless to the human body when used for packaging food, and recyclable as a raw material for making paper. It is also biodegradable and therefore, environment-friendly.

12 Claims, 16 Drawing Sheets

FIG. 14

| Test Results for RP202 |||||
|---|---|---|---|---|
| Solvent | Residue (mg/in$^2$) | Chloroform Residue (mg/in$^2$) | Criteria (mg/in$^2$) | Pass/Fail |
| Purified Water A | 0.08 | N/A | 0.5* | Pass |
| Purified Water B | 0.06 | N/A | 0.5* | Pass |
| Purified Water C | 0.07 | N/A | 0.5* | Pass |
| Purified Water D | 0.11 | N/A | 0.5* | Pass |
| Heptane A | 0.01 | N/A | 0.5* | Pass |
| Heptane B | 0.02 | N/A | 0.5* | Pass |
| Heptane C | 0.01 | N/A | 0.5* | Pass |
| Heptane D | 0.01 | N/A | 0.5* | Pass |
| 8% Alcohol A | 0.11 | N/A | 0.5* | Pass |
| 8% Alcohol B | 0.13 | N/A | 0.5* | Pass |
| 8% Alcohol C | 0.09 | N/A | 0.5* | Pass |
| 8% Alcohol D | 0.11 | N/A | 0.5* | Pass |

*Most stringent criteria of 0.5 mg/in$^2$ was used since information was not provided for intended use of the sample.

FIG. 15

Test result(s):
US FDA 21 CFR 176.170 – (Paper and Paperboard)
Determination of Amount of Net Chloroform Soluble Extractives Method: With reference to US FDA 21 CFR 176.170 on Table 2 (A)

| Extractants | Test Condition | Result (mg/inch$^2$) | Detection Limit (mg/inch$^2$) | Permissible Limit (mg/inch$^2$) |
|---|---|---|---|---|
| Distilled Water | 250 °F for 2 hours | N.D | 0.2 | 0.5 |
| 8% Alcohol | 150 °F for 2 hours | N.D | 0.2 | 0.5 |
| 50% Alcohol | 150 °F for 2 hours | N.D | 0.2 | 0.5 |
| n-Heptane | 150 °F for 2 hours | N.D | 0.2 | 0.5 |
| Comment | -- | PASS | -- | -- |

Note: 1. mg/inch$^2$ = milligram per square inch
2. °F = degrees Fahrenheit
3. N.D = Not detected

FIG. 16

Phthalates

| Analysis item | Unit | Test method | Detection limit | Result |
|---|---|---|---|---|
| Di-(2-ethylhexyl) phthalate (DEHP) | mg/kg | With reference to EPA 8061A, GC/MS | 50 | Not detected |
| Di-butyl phthalate (DBP) | mg/kg | With reference to EPA 8061A, GC/MS | 50 | Not detected |
| Benzyl butyl phthalate (BBP) | mg/kg | With reference to EPA 8061A, GC/MS | 50 | Not detected |
| Di-isobutyl phthalate (DIBP) | mg/kg | With reference to EPA 8061A, GC/MS | 50 | Not detected |
| Di-isodecyl phthalate (DIDP) | mg/kg | With reference to EPA 8061A, GC/MS | 50 | Not detected |
| Di-isononyl phthalate (DINP) | mg/kg | With reference to EPA 8061A, GC/MS | 50 | Not detected |
| Di-n-octyl phthalate (DNOP) | mg/kg | With reference to EPA 8061A, GC/MS | 50 | Not detected |

PAPER COATING MATERIAL HAVING ENVIRONMENT-FRIENDLY, WATER-PROOF AND OIL-PROOF PROPERTIES, AND METHOD OF MANUFACTURING THE SAME

This application claims the priority of Korean Patent Application No. KR10-2016-0126701 filed on Sep. 30, 2016. The entire disclosure of the above application is incorporated herein by reference.

BACKGROUND

The present invention relates to a paper coating material, and a method of manufacturing the same, and more specifically, to a paper coating material which is recyclable and thus environment-friendly, and which has moisture-proof, water-poof, and oil-proof properties, and to a method of manufacturing the same.

In 1907, Houg Moor from the USA invented paper cups and advertised that only disposable cups could ensure the protection of human beings from bacteria. Since then, people have used paper cups over 100 years because paper cups are hygienic and convenient for use.

Paper food containers such as paper cups should be water-proof since the basic role thereof is to put water and a drink therein. Currently, most of paper cups are manufactured by coating or laminating paper with polyethylene (PE). Paper or paper cups coated with polyethylene are excellent in water-proof property and are advantageous for mass production.

However, in reality, there are many problems in recycling paper cups coated with polyethylene instead of disposing the paper cups. That is, in a process of removing polyethylene from the paper cups to be recycled, pulp fiber of paper is damaged and stiffens. Also, in a process of removing polyethylene, it is necessary to separate paper and polyethylene. However, most of polyethylene is not dissociated well in an alkaline solution such as sodium hydroxide, and moreover, it is only partially dissociated even in an alkaline solution at a boiling temperature. When recycling paper having polyethylene not dissociated but still adsorbed thereonto, paper coming out of a papermaking machine sticks to the periphery of a roller when going through a drying process of high temperature. This causes the quality of the paper to be significantly lowered, and therefore, most of the paper can only be recycled as low-quality paper such as toilet paper.

As the demand for environment-friendly paper coating material has grown, there have been many attempts of research and development. Korean Patent No. 10-1089765 discloses a method of manufacturing paper coating material having basic properties, such as water-proof, oil-proof, and heat sealing properties, and an environment-friendly property, by coating copolymer latex having a core-shell structure through a conventional papermaking facility. Since the copolymer latex disclosed above is alkali-dissociable, the recycling possibility is predicted. However, due to the inherent physical properties of copolymer latex, a blocking phenomenon in which paper rolls stick to each other during the manufacturing process at high temperature under high pressure occurs, which makes it difficult to apply to the mass production in the actual papermaking process.

Korean Patent No. 10-1100954 discloses food wrapping paper with an emphasis on environment-friendliness that is produced through a method of coating paper with a coating liquid prepared by mixing a fluorine-based oil-proof agent and polyvinyl alcohol (PVA). However, since polyvinyl alcohol itself is hygroscopic, when the water absorption in food wrapping paper becomes large, the blocking property thereof sharply decreases and the water resistance is deteriorated. Korean Patent 10-1329259 discloses wrapping paper with improved water repellency and oil-proof property by applying, to kraft paper, a coating liquid prepared by mixing starch, paraffin wax emulsion, or polyethylene emulsion. However, moisture permeation over a long period of time could not be prevented.

Paper food containers can be substantially an environment-friendly alternative only if the paper food containers have water-proof, oil-proof, and heat sealing properties and can be readily manufactured even by a conventional papermaking machine. In addition, price competitiveness is essential to replace conventional paper products coated with polyethylene. Environment-friendly paper coating material with such multi-competitiveness has not yet been developed.

Therefore, the present inventor has studied for a long time to solve such a problem and finally developed and completed the present invention through trial and error

SUMMARY

An object of the present invention is to provide a paper coating material which is environment-friendly because the paper coating material is recyclable and has excellent moisture-proof, oil-proof, and water-proof properties.

Another object of the present invention is to provide a method of manufacturing such a paper coating material.

Objects of the present invention are not limited to the above-mentioned objects, and other unmentioned objects may be clearly understood by those skilled in the art from the following description.

According to an embodiment of the present invention to achieve the object, a paper coating material includes: a copolymer emulsion in which a silicon-based polymer having a repeating unit represented by formula 1 below and an acryl-based polymer having a repeating unit represented by formula 2 below are copolymerized, wherein particles included in the copolymer emulsion have a weight average molecular weight of 100,000 to 200,000; and a colloidal aqueous solution of gelatinized polyvinyl alcohol to be mixed with the copolymer emulsion.

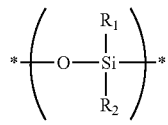
[Formula 1]

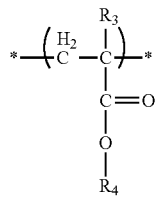
[Formula 2]

(in formulae 1 and 2 above, R1 to R4 may be same or different, and are each independently hydrogen, or a substituted or unsubstituted alkyl group or aryl group).

The weight ratio between the acryl-based polymer and the silicon-based polymer may be 99:1 to 99.9:0.1.

The weight ratio between the copolymer emulsion and the colloidal aqueous solution of polyvinyl alcohol may be 85:15 to 95:5 based on a solid content.

The glass transition temperature of the copolymer emulsion may be 300 to 340° C.

The degree of saponification of the polyvinyl alcohol may be 92 to 99 mol %.

According to an embodiment of the present invention to achieve another object, a method of manufacturing a paper coating material includes the steps of, (a) adding, to a reactor, water, acryl-based monomer, an initiator, an emulsifier, a buffer, and a silicon reaction catalyst; (b) adding a silicon-based monomer to the reactor at a uniform rate; (c) producing a copolymer emulsion having a weight average molecular weight of 100,000 to 200,000 by adjusting the temperature of the reactor; (d) putting water and polyvinyl alcohol into a separate container and stir to prepare a colloidal aqueous solution of gelatinized polyvinyl alcohol; and (e) adding the colloidal aqueous solution of gelatinized polyvinyl alcohol to the copolymer emulsion.

The weight ratio between an acryl-based polymer and a silicon-based polymer included in the copolymer emulsion may be 99:1 to 99.9:0.1.

The weight ratio between the copolymer emulsion and the colloidal aqueous solution of polyvinyl alcohol may be 85:15 to 95:5 based on a solid content.

The silicon reaction catalyst may be dibutyl tin dilaurate (DBTDL).

The colloidal aqueous solution of gelatinized polyvinyl alcohol may be prepared by adding 7 to 15 wt % of polyvinyl alcohol into water and stirring for 1 to 10 minutes at a temperature of 85 to 98° C.

The glass transition temperature of the copolymer emulsion may be 300 to 340° C.

The degree of saponification of the polyvinyl alcohol may be 92 to 99 mol %.

In step (a), the temperature of the reactor may be maintained at 50 to 70° C., and in the step (c), the temperature of the reactor may be maintained at 70 to 90° C.

Specific details of other embodiments are included in the following description and drawings.

As described above, paper products using a paper coating material according to the present invention have excellent water-proof, oil-proof, and heat sealing properties, and are harmless to human bodies when used as food packaging containers or paper cups. Coated paper products are recyclable as a raw material for paper, and are environment-friendly since the coating material is bio-degradable. The paper coating material according to the present invention may be used for paper products as the paper coating material can be readily applied even in a conventional production facility, and the additional modification is possible to meet market needs. Furthermore, when using the paper coating material of the present invention, it can be expected to achieve cost reduction since manufacturing costs are not high compared to that of a polyethylene coating material.

When coating base paper with the paper coating material according to the present invention, the efficiency of copolymerization of an acryl-based monomer and a silicon-based monomer is excellent such that the amount of unreacted monomer in the coating material is very small. Furthermore, unreacted monomers remaining in the copolymer emulsion are vaporized in the air through a purification process, and chemical odors may thus be completely eliminated which may be caused by the unreacted monomers.

BRIEF DESCRIPTION OF THE DRAWINGS

FIG. 14 shows the results of experiment obtained by requesting a US certification company (UL Verification Services, Inc.) to perform the experiment on the coated paper of the present invention.

FIG. 15 shows the results of experiment obtained by requesting a global certification company (SGS) to perform the experiment on the coated paper of the present invention.

FIG. 16 is a graph showing the results of experiment regarding whether to detect phthalate, an environmental hormone, by requesting a global certification company (SGS) to perform the experiment on the coated paper of the present invention.

DETAILED DESCRIPTION OF PREFERRED EMBODIMENTS

Figure 1:
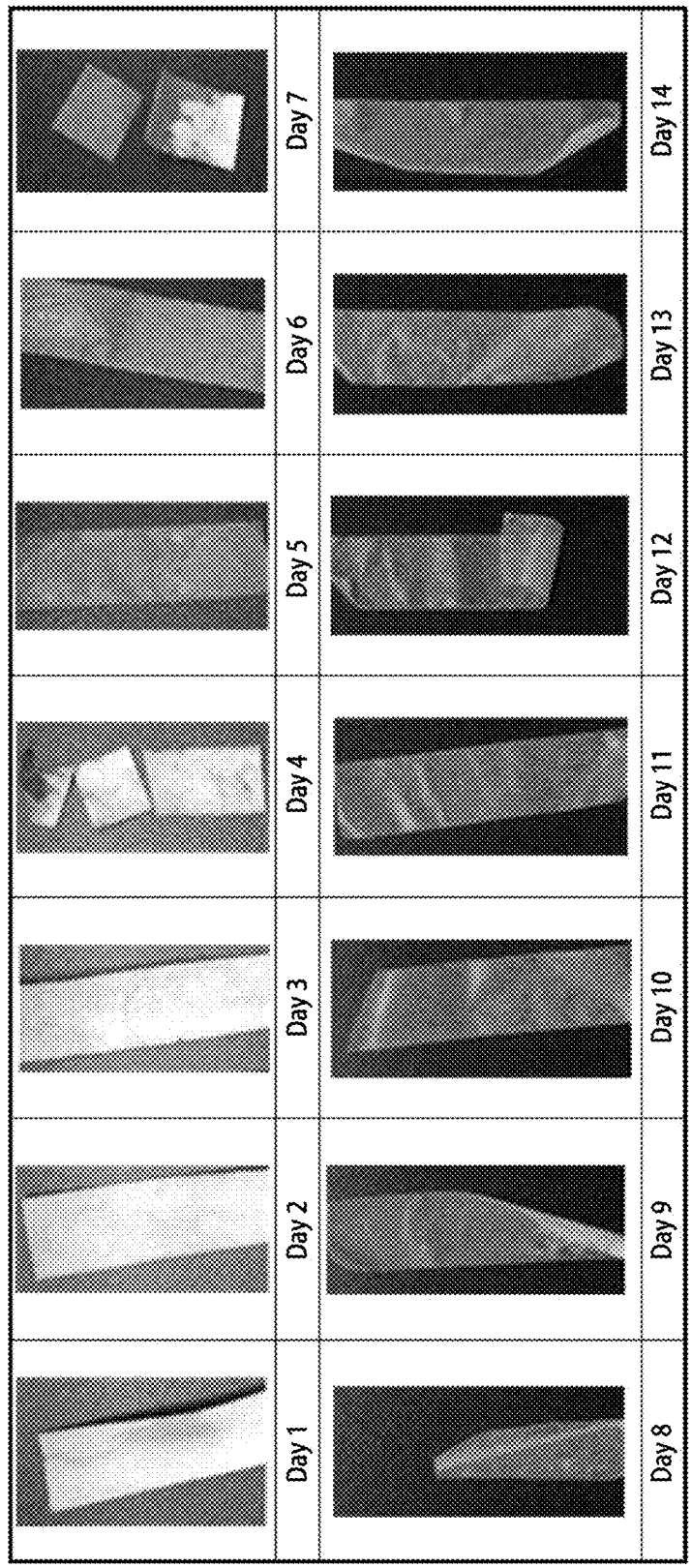
FIG. 1 is a photograph showing a biodegradation process of coated paper (Comparative Example 1) observed for 14 days, wherein the coated paper uses a conventional PE coating material.

The advantages and features of the present invention, and the manner of achieving them, will become apparent with reference to the embodiments described in detail below with reference to the accompanying drawings. The present invention may, however, be embodied in many different forms and should not be construed as being limited to the embodiments set forth herein. Rather, these embodiments are provided so that this disclosure will be thorough and complete, and will fully convey the concept of the invention to those skilled in the art. It is intended to give the possessor a complete indication of the scope of the invention and the invention is only defined by the scope of the claims. Like reference numerals refer to like elements throughout the specification.

Hereinafter, the present invention will be described in detail.

<Paper Coating Material>

An environment-friendly paper coating material of the present invention includes: a copolymer emulsion in which a silicon-based polymer having a repeating unit represented by formula 1 below and an acryl-based polymer having a repeating unit represented by formula 2 below are copolymerized; and a colloidal aqueous solution of gelatinized polyvinyl alcohol which is mixed with the copolymer emulsion.

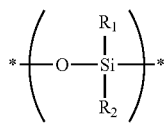

[Formula 1]

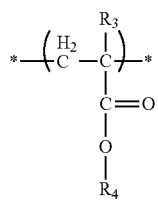

[Formula 2]

In formulae 1 and 2 above, R1 to R4 may be the same as or different from each other, and are each independently hydrogen, or a substituted or unsubstituted alkyl group or aryl group. The R1 to R4 may include an R group shown in Table 1 below, but the present invention is not limited thereto, and may be selected according to the molecular weight range of the copolymer emulsion. Table 1 shows possible forms of R1 to R4 in formula 1 and formula 2.

TABLE 1

| R Group | Name | Abbreviations | Class |
|---|---|---|---|
| —H | Glycine | Gly, G | Aliphatic |
| —CH$_3$ | Alanine | Ala, A | |
| —CH(CH$_3$)$_2$ | Valine | Val, V | |
| —CH$_2$CH(CH$_3$)$_2$ | Leucine | Leu, L | |
| —CHCH$_3$CH$_2$CH$_3$ | Isoleucine | Ile, I | |
| —CH$_2$OH | Serine | Ser, S | Hydroxyl or sulfur containing |
| —CHOHCH$_3$ | Threonine | Thr, T | |
| —CH$_2$SH | Cysteine | Cys, C | |
| —(CH$_2$)$_2$SCH$_3$ | Methionine | Met, M | |
| —CH$_2$COOH | Aspartic acid | Asp, D | Acids and corresponding amides |
| —CH$_2$CONH$_2$ | Asparagine | Asn, N | |
| —(CH$_2$)$_2$COOH | Glutamic acid | Glu, E | |
| —(CH$_2$)$_2$CONH$_2$ | Glutamine | Gln, Q | |
| —(CH$_2$)$_3$CH$_2$NH$_2$ | Lysine | Lys, K | Basic |
| —(CH$_2$)$_3$NHCNHNH$_2$ | Arginine | Arg, R | |
| —CH$_2$–[imidazole] | Histidine | His, H | |
| —CH$_2$–[phenyl] | Phenylalanine | Phe, F | Aromatic |
| —CH$_2$–[phenyl]—OH | Tyrosine | Tyr, Y | |
| —CH$_2$–[indole] | Tryptophan | Try, W | |
| [pyrrolidine]—COOH | Proline | Pro, P | Imino acid |
| —CH$_2$—S—S—CH$_2$— | Cystine | — | Disulfide |

In the copolymer emulsion of the present invention, the weight ratio between the silicon-based polymer and the acryl-based polymer is preferably 0.1:99.9 to 1:99. Here, if the weight ratio of the silicon-based polymer is greater than 1, releasability is too high, thereby causing cracks on an adhesive surface when making paper. On the other hand, if the weight ratio of the silicon-based polymer is less than 0.1, adhesiveness is too high, thereby causing a blocking phenomenon in which paper products stick to each other to result in a significant decrease in productivity. The glass transition temperature of the copolymer emulsion has a range of 300 to 340° C., preferably 310 to 330° c. The weight average molecular weight of the particles included in the copolymer emulsion is in a range of 100,000 to 200,000. Here, if the weight average molecular weight is less than 100,000, the coating material has good sealability, but is too sticky to be unsuitable for mass production. If the weight average molecular weight is greater than 200,000, the waterproof and heat-resistant properties of the coating material are improved but the sealability thereof is reduced. The average diameter of the particles included in the copolymer emulsion is 150 to 250 nm. The copolymer emulsion is a water-soluble emulsion having a solid content of 35 to 50 wt %, and may have a viscosity of 5 to 600 cPs. If the concentration of the copolymer emulsion is less than 35 wt %, the water-proof property is reduced such that the function thereof as a container for containing a liquid is lost, and heat sealing property is also reduced, resulting in a defect in molding the paper container. If the concentration of the copolymer emulsion is greater than 50 wt %, the adhesive strength is too strong thereby causing a blocking phenomenon in which paper products stick to each other.

The acryl-based monomer that may be used in the present invention may include one or more compounds selected from the group consisting of methyl acrylate, ethyl acrylate, 2-hydroxyethyl acrylate propyl acrylate, butyl acrylate, 2-ethylhexyl acrylate, cyclohexyl acrylate, methyl methacrylate, ethyl methacrylate, hydroxyethyl methacrylate, propyl methacrylate, n-butyl methacrylate, cyclohexyl methacrylate, isobutyl methacrylate, acrylonitrile, methacrylic acid, and a combination thereof. Preferably, the acryl-based monomer may include a combination of butyl acrylate, methyl methacrylate, hydroxyethyl methacrylate, and methacrylic acid.

The silicon-based monomer that may be used in the present invention may include a cyclosiloxane compound selected from the group consisting of hexamethylcyclotrisiloxane, octamethylcyclotetrasiloxane, decamethylcyclopentasiloxane, dodecamethylcyclohexasiloxane, trimethyltriphenylcyclotrisiloxane, tetramethyltetraphenylcyclotetrasiloxane, octaphenylcyclotetrasiloxane, and a combination thereof.

The polyvinyl alcohol that may be used in the present invention preferably has a high degree of saponification in order to enhance the property of blocking water vapor or gas. For example, the degree of saponification of the polyvinyl alcohol may be 92 to 99 mol %. Based on the solid content, the copolymer emulsion and the colloidal aqueous solution of polyvinyl alcohol may be included at a weight ratio of 85:15 to 95:5. If the amount of the polyvinyl alcohol is greater than 15 wt %, a coating layer is too hardened after the coating material is applied to paper, thereby causing small cracks, resulting in the deterioration of blocking effect. On the other hand, if the amount of the polyvinyl alcohol is less than 5 wt %, the water-proof and moisture-proof properties are reduced due to insufficient amounts of active ingredients for giving a blocking effect.

<A Method of Manufacturing the Paper Coating Material of the Present Invention>

A method of manufacturing the paper coating material according to the present invention is as follows. The method of manufacturing the paper coating material of the present invention was carried out by adopting a monomer addition process.

(1) Add an acryl-based monomer, an initiator, an emulsifier, a buffer, and a silicon reaction catalyst while maintaining a water-containing reactor at 50 to 70° C.

(2) Add an initiator while maintaining the reactor at 70 to 90° C.

(3) Prepare a copolymer emulsion by adding, to the resultant product, a silicon-based monomer at a uniform rate for 1 to 3 hours and carrying out a copolymerization reaction.

(4) After the completion of the copolymerization reaction, add a post-additive to carry out neutralization.

(5) Add a colloidal aqueous solution of gelatinized polyvinyl alcohol to the copolymer emulsion.

The copolymerization efficiency of the present invention may be improved by making the reactor have different temperatures in step (1) and step (2). If the temperature of the reactor in step (1) is lower than 50° C., the reactivity of the added materials is low such that it is difficult to increase the subsequent copolymerization reaction rate. Also, if the temperature of the reactor in step (1) is higher than 70° C., the polymerization reaction between the acryl-based monomers starts to reduce the reaction rate of copolymerization of the acryl-based monomers and the silicon-based monomers. Thus, by preparing step (1) at a temperature lower than the optimum temperature range (70 to 90° C.) for copolymerization as in step (2), the amount of unreacted monomers may be minimized and copolymerization efficiency may be increased. As such, the temperature of the reactor is adjusted such that the weight average molecular weight of the particles included in the copolymer emulsion is 100,000 to 200,000.

Hereinafter, the components used in the manufacturing method will be described.

Water

The role of water in emulsion polymerization is very large and important, and the physical properties of the prepared emulsion are highly dependent on the quality of the water. Water is a dispersion medium of a material to be emulsified, which facilitates heat transfer during polymerization, and also acts as a solvent for an emulsifier, a monomer, and an initiator. In addition, the viscosity of the emulsion is adjusted by water, and a relatively high solid content and a low viscosity are one of the great advantages of the emulsion. Since there are many polyvalent metal ions in natural water, it is preferable to use ion exchanged water having very small contents of ions and salts. For example, in this experimental example, deionized water was used.

Initiator

When the initiator is decomposed, free radicals that cause a reaction are generated. In the present invention, a water-soluble initiator may be used, and persulfate or hydrogen peroxide may be used. For example, potassium persulfate, sodium persulfate, or ammonium persulfate may be used.

Emulsifier

The emulsifier is a surfactant and is indispensable for emulsion polymerization. The emulsifier forms swollen particles with micelles or monomers in the beginning of a reaction, and thus provides a place where the reaction may take place. In addition, the emulsifier serves to protect monomer droplets and stabilizes the source of monomer. As the reaction progresses, the particles become larger and the size of monomer droplets becomes smaller, such that the emulsifier moves from the particles of monomer to the surface of particles. For example, octyl phenol ethoxylate (OP), nonyl phenol ethoxylate (NP), ethylene oxide (EO), sodium dodecyl sulfate (SDS), or a combination thereof may be used as an emulsifier.

Buffer

In the copolymerization of the present invention, the reaction proceeds under acidic conditions. The buffer serves to stabilize the pH during the copolymerization reaction and maintains the solubility of the initiator. In the present invention, $Na_2CO_3$, $NaHCO_3$, $(NH_4)_2CO_3$, $NaH_2PO_4$, $Na_2HPO_4$ and the like may be used as a buffer.

Silicon Reaction Catalyst

In the copolymerization of the present invention, the silicon reaction catalyst may be used to promote the copolymerization reaction of the acryl-based monomer and the silicon-based monomer and also promote the polymerization reaction of the silicon-based monomer. For example, dibutyltin dilaurate (DBTDL) may be used as a silicon reaction catalyst.

Post-Additive

Various additives may be added for the pH, the viscosity, or other properties of the reacted copolymer emulsion. In the present invention, after the completion of the copolymerization reaction, the post-additive is added to increase the pH, thereby imparting stability to the copolymer emulsion and preventing an unnecessary secondary reaction. For example, ammonia water may be used as a post-additive in the present invention.

Colloidal Aqueous Solution of Polyvinyl Alcohol 7 to 15 wt % of polyvinyl alcohol is added to water and stirred at 85 to 98° C. for 1 to 10 minutes to prepare a colloidal aqueous solution of polyvinyl alcohol which is gelatinized (gelatinization: a state in which micelles are swollen and changed into colloid) and the colloidal aqueous solution thus obtained is introduced into the copolymer emulsion. When the polyvinyl alcohol not being gelatinized is introduced into the copolymer emulsion, the polyvinyl alcohol is not mixed with the copolymer emulsion but forms a separation membrane. Based on a solid content, the copolymer emulsion and the colloidal aqueous solution of polyvinyl alcohol may be added at a weight ratio of 85:15 to 95:5. Polyvinyl alcohol having a high degree of saponification has excellent oil-proof, water-proof, and moisture-proof properties. Preferably, the degree of saponification of polyvinyl alcohol is 92 to 99 mol %. Particularly, when polyvinyl alcohol is mixed with an acrylic-silicon copolymer, the polyvinyl alcohol penetrates between the sparse molecular structure of the acryl-based polymer and serves to prevent the permeation of moisture.

<A Method of Manufacturing Environment-Friendly Paper Using the Paper Coating Material>

Hereinafter, a method of manufacturing environment-friendly paper using the paper coating material of the present invention will be described.

The term "paper" that is used in the present invention encompasses both base paper for paper cups and paper for food packaging, which are typically produced and marketed in the paper industry. In addition, the paper may be paper in which food safety is ensured.

Paper used in the present invention may be paper having a basis weight of 80 to 400 g/m² among various types of base paper or food packaging paper (uncoated base paper for paper cups) produced and distributed in the paper industry. Base paper having a basis weight of less than 80 g/m² is low in thickness and strength such that it is difficult to maintain the shape and water-proof property thereof when molded into a cup or a food container. Base paper having a basis weight of greater than 400 g/m² is difficult to be produced in a single process by using a conventional paper making facility, and is not commonly used. Meanwhile, it is desirable to avoid use of waste paper which may be used as a raw material collected for recycling as a raw material for paper cups or paper food containers in consideration of the safety of food packaging. However, based on the papers specifications of the Food and Drug Administration's 2013 notification "Standard for Apparatus, Containers and Packaging for Food", a representative standard for testing harmlessness of paper in the form of final paper and processed paper, within the scope of obtaining test results below the reference value of arsenic, lead, formaldehyde, and fluorescent whitening agents and the like, recycled waste paper may be used in a certain amount as being mixed with natural pulp.

Prepared is base paper for food which is not coated and has a basis weight of 80 to 400 g/m². The inner surface (the surface touching food) of the base paper is coated with 4 to 20 g/m² of an environment-friendly coating material based on a solid content. Here, if the coating amount of the coating material is less than 4 g/m², it is difficult to exhibit the water-proof and heat sealing properties thereof, and the oil-proof property is reduced since a coating film is thin and uneven. In addition, if the coating amount of the coating material is greater than 20 g/m²' a blocking phenomenon in which paper sticks to each other occurs and the releasability of the coating material is increased, such that the coating film may be cracked when dried excessively.

The method of manufacturing environment-friendly paper may further include the step of coating the outer surface of the base paper (the surface not touching food) with the environment-friendly coating material in an amount of 0.1 to 5 g/m² based on a solid content of the coating material. In other words, it is sufficient to apply the coating material only on the inner surface where the food is in contact, but for a paper container to be applied to cold drinks or refrigerated foods, it is also possible to apply the coating material to the outer surface of the base paper thereof. When paper is used for manufacturing a cup for cold drinks, or wrapping paper for refrigeration in summer usually, water vapor condenses on the outer surface of the paper container due to the temperature difference between both sides of the paper. This condensation makes the paper container wet. When the coating material is applied to the outer surface, the condensation phenomenon and the wetting phenomenon are prevented. If the coating material is used in an amount of less than 0.1 g/m², the thickness of the applied coating material is too small to have a waterproof effect on the outer surface, and if the coating material is used in an amount of greater than 5 g/m², the printability of the outer surface is deteriorated.

Such coating methods may be performed by using a conventional coating facility used in the paper industry. The coating facility for coating may employ either an on-machine coater or an off-machine coater of the paper industry. The coating method of the present invention may be performed by using any one selected from the group consisting of a roll coater, a blade coater, a rod coater, an air knife coater, a short dwell coater capable of effectively controlling a low coating amount, a bill blade coater, and a gate roll coater. Also, the same coating effect may be obtained in a gravure type printing facility.

The environment-friendly paper having water-proof, oil-proof and heat sealing properties by applying the coating material of the present invention may be subjected to a post-processing for enhancing the merchantability. For example, in order to improve printability, a conventional pigment coating for papermaking may be applied to the outer surface of the paper. Substances constituting the paper coating material of the present invention are harmless and food-stable which may be used in the food packaging industry. In addition, since a manufacturing process of the paper coating material and a manufacturing method of paper using the same are both performed in an aqueous environment, and are thus environment-friendly.

Paper containers coated with the paper coating material of the present invention is alkali-dissociable, and may thus be collected after use and recycled as a raw material for paper. Furthermore, when compared with a conventional polyethylene coating material, the paper coating material of the present invention has a superior bio-degradation rate, so that there is less burden on the environmental destruction even if the paper coating material is buried after use.

Hereinafter, preferred embodiments of the present invention will be described in detail with reference to the accompanying drawings. It is to be understood, however, that these examples are offered by way of illustration only, and the scope of the present invention is not limited to these examples.

EXAMPLE 1

Preparation of a Paper Coating Material Including Polyvinyl Alcohol and a Copolymer Emulsion in which a Silicon-based Polymer and an Acryl-based Polymer are Copolymerized While maintaining the temperature of a reactor containing 120 g of deionized water at 60° C., an acryl-based monomer mixture prepared by mixing 40 g of methyl methacrylate, 44 g of butyl acrylate, 1.0 g of methacrylic acid, and 1.0 g of hydroxyethyl methacrylate was added to the reactor. 0.2 g of ammonium persulfate, 0.4 g of dibutyl tin dilaurate (DBTDL), 1.0 g of octyl phenol ethoxylate (OP), 0.8 g of sodium dodecyl sulfate (SDS) and 0.2 g of $Na_2CO_3$ were added thereto.

When the temperature of the reactor reached 80° C., ammonium persulfate was added. After 10 minutes, a silicon-based monomer was introduced into the reactor at a uniform rate over a period of 2 hours. The amount of the silicon-based monomer was controlled such that the weight ratio of the acryl-based polymer and the silicon-based polymer in the copolymer emulsion was 99 to 99.9:0.1 to 1.

After the completion of the copolymerization, ammonia water was added to neutralize the copolymer emulsion such that the solid content of the copolymer emulsion became 35 to 50 wt %. After this, the resulting reactant was purified. The unreacted monomer remaining in the copolymer emulsion was vaporized into the air through the above purification process to completely remove the chemical odor which may often be present in the paper coating material.

In the meantime, 7 to 15 wt % of polyvinyl alcohol based on the total aqueous solution is added to water and stirred at 85 to 98° C. for 1 to 10 minutes to prepare a colloidal aqueous solution of gelatinized polyvinyl alcohol. The colloidal aqueous solution of polyvinyl alcohol is added to the purified copolymer emulsion. Based on a solid content, the weight ratio of the copolymer emulsion to the colloidal aqueous solution of polyvinyl alcohol was 85:15 to 95:5. In this embodiment, RS-2117 manufactured by Kuraray Co., Ltd. of Japan was used as the polyvinyl alcohol. Finally, a paper coating material was prepared.

EXAMPLE 2

Preparation of a Coating Material, and Coating of Base Paper for Cups

Wrapping paper was coated with the paper coating material prepared according to the preparation method of Example 1. A base paper for a cup manufactured by Hansol Paper Co., Ltd. (trade name: FAB350, basis weight: 350 g/m$^2$) was used. A water-soluble coating liquid in which 35.0 wt % of solids of the paper coating material of the present invention, 0.2 wt % of silica, and 64.8 wt % of water were mixed was applied to perform a single-sided coating at 9.5 g/m$^2$ using an air knife type coating facility.

EXAMPLE 3

Coating of Base Paper for Cups

The same base paper for cups and coating liquid as in Example 2 were applied to perform a single-sided coating at 8.5 g/m$^2$ using a rod-type coating facility.

COMPARATIVE EXAMPLE 1

Cup Paper Coated with Polyethylene Coating Material

Polyethylene-coated cup paper (basis weight 350 g/m$^2$) distributed in the cup molding market was used as Comparative Example 1.

COMPARATIVE EXAMPLE 2

Cup Paper Coated with Polylactic Acid (PLA)

Polylactic acid-coated cup paper (basis weight 350 g/m$^2$) distributed in the cup molding market was used as Comparative Example 2.

COMPARATIVE EXAMPLE 3

Uncoated Cup Paper

The same base paper for cups as in Example 2 was used as Comparative Example 3 without coating.

EXPERIMENTAL EXAMPLE 1

Test for Physical Properties

The physical properties of materials which were prepared through Examples and Comparative Examples were tested under the same conditions, and the results are shown in Table 2 and compared.

Cup paper or food packaging paper coated with the paper coating material according to an embodiment of the present invention exhibited suitable physical properties such as water-proof, oil-proof, heat sealing properties, for a food container containing moisture and oil. When the oil-proof property was tested by the US Paper Pulp Technology Association test method (TAPPI T559 cm-02), kit #4 or higher was achieved. As for the water-proof property, when applied with the so-called Cobb size test method (TAPPI T441), which is one of the conventional methods in the papermaking industry, 10.0 g/m² or less of water-proof property was shown. The heat adhesive strength was determined by using a heat sealing device (Sambo Tech, SK-310) and heat sealing was performed at the sealing strength of 5. When 180-degree peeling test was conducted with a peel tester, the peel strength of the adhesive layer was 300 gf/in or more.

However, since the test according to the standard test method is insufficient to fully evaluate the possibility of mass production in a conventional cup molding facility, water-proof and oil-proof properties were additionally observed as follows. First, cup paper was molded by using the paper coating material of the present invention under the normal production conditions with a cup molding facility using a heat compression method and a high frequency adhesive method. The adhesive surface thereof was peeled off again to visually observe the level of heat sealing, and then the cup paper contained a liquid content in which a water-based coloring agent was mixed with milk and soapy water for 48 hours. The water-proof and oil-proof properties were additionally observed visually at room temperature.

In addition, in order to examine the environment friendliness, a test for dissociation was carried out based on the Environmental Mark Certification Standard (EL606) conducted by the Korea Environmental Industry & Technology Institute, and the presence or absence of residual impurities and adhesive property were determined. As a result, the paper coating material of the present invention exhibited alkali-dissociable property, and it was confirmed that a paper container coated with the coating material of the present invention may be collected and recycled as a raw material for paper after use. In addition, biodegradability is expressed as a percentage by the ratio of the change in the degree of biodegradation of the sample and the standard substance for 180 days in accordance with KS M3100-1. As a result, it was confirmed that the paper container coated with the coating material of the present invention had aerobic biodegradability under composting conditions.

In addition, the coated paper of the present invention showed the results conforming to the test standards of the paper material and coated paper material of the Korea Food and Drug Administration Food Code "Article 7, the criteria and standards for equipment and container packaging", which was announced in 2013.

TABLE 2

| Item | Measurement method | Example 2 | Example 3 | Comparative Example 1 | Comparative Example 2 | Comparative Example 3 |
| --- | --- | --- | --- | --- | --- | --- |
| Oil-proof property Kit# | TAPPI T559cm-02 | 5 | 4 | 4 | 4 | None |
| Water-proof property g/m²/2 minute | Cobb Size TAPPI T441 | 9.5 | 7.7 | 9.6 | 8.9 | 21.9 |
| Heat sealing strength gf/inch | peel tester | 340 | 340 | 360 | 330 | Not Applicable |
| Molding facility high frequency adhesive property | Visually determined after forced separation | Paper peeled off also | Paper peeled off also | Paper peeled off also | Coated side peeled off | Not Applicable |
| Milk and soapy water leakage | Visually determined after 48 hours | No leaks | No leaks | No leaks | No leaks | Not Applicable |
| Molding defect rate | 5000 thousands defective molding number | 0 | 0 | 0 | 3 | Not Applicable |
| Dissociation property | EL606 | Dissociated | Dissociated | Not Dissociated | Not Dissociated | Dissociated |
| Biodegradable property % | KS M3100-1 | 84 | 85 | 55 | 86 | 85 |

From the results shown in Table 2, it may be seen that the environment-friendly cup paper manufactured by the methods of Examples 2 to 3 according to the present invention exerts excellent performance as a food packaging material having environment-friendly, water-proof, oil-proof, and heat sealing properties.

EXPERIMENTAL EXAMPLE 2

Test for Biodegradability Comparison

<2-1> Preparation of a Sample

A precision test for biodegradability was conducted on the coated paper (Comparative Example 1) prepared by using polyethylene (PE) as an internal coating material, which is most commonly distributed in the market, and the coated paper (Example 2) prepared according to the manufacturing method of the present invention (here, cup paper coated with a coating material is abbreviated as coated paper). The anaerobic microorganisms used for the test for biodegradability were anaerobic sludge received from Daejeon sewage treatment plant.

<2-2> Experiment Method

Each sample cut to a specific size (1.5 cm×6.5 cm) was prepared. Before examining the biodegradability using the anaerobic microorganisms, UV (254 nm wavelength) was irradiated to each sample for 6 hours using an UV cross-linker (UVP, CL-100) to promote oxidative degradation of the coating material. Then, samples were divided into two groups, one irradiated with UV, and the other with no irradiation. The samples were anaerobically incubated for 14 days in an incubator controlled at a speed of 200 rpm at a temperature of 38° C. C. The samples then were taken out at intervals of one day, washed, and dried at a temperature of 60° C.

<2-3> Biodegradability Analysis Method

A thickness meter (model: L&W micrometer, Lorentzen & Wettre, Sweden) was used to measure the thickness of a coating film and the coated paper of each sample. The thickness of the coating film was determined by inflating the coated paper in water, removing the base paper, and using the remaining coating film. The degree of degradation of each sample by time was observed with the naked eye. Also, to observe microstructural changes of the coated paper, a stereomicroscope (Leica EZ4 HD) was used. The specific peaks of the inner coating material of the coated paper were analyzed using FT-IR (VERTEX 70, Bruker Optics, Germany) to analyze the structural changes of the coated paper due to the biodegradation. In order to confirm the change in the physical surface properties of each coated paper, samples were taken out for each period of degradation, dried completely, and 10 μl of distilled water was dropped on each coated paper to measure the contact angle of hydration.

<2-4> Measurement of the Thickness of Coated Paper

Table 3 below shows the results of measuring the thickness of the coated paper of Comparative Example 1 (PE coating) and the coated paper of Example 2.

TABLE 3

|  | Example 2 | Comparative Example 1 |
| --- | --- | --- |
| Thickness of coated paper (μm) | 251.14 ± 0.47 | 269.12 ± 1.54 |
| Thickness of coating film (μm) | 47.84 ± 3.24 | 33.64 ± 1.60 |

The coated paper of Comparative Example 1 was thicker than the coated paper of Example 2. However, the coating film of Example 2 was slightly thicker than the coating film of Example 2.

<2-5> Observation of the Biodegraded Coated Paper with the Naked Eye

Figure 2:
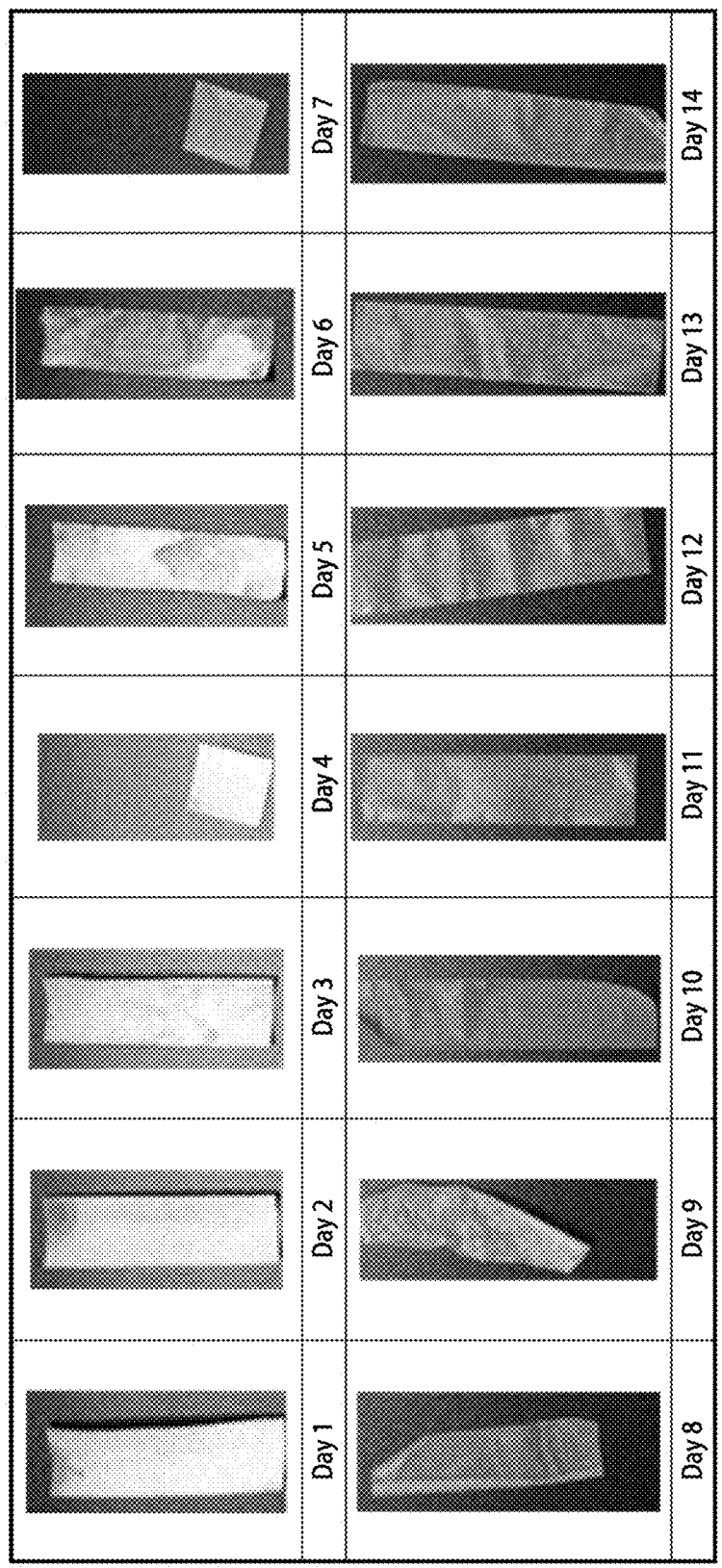
FIG. 2 is a photograph showing a biodegradation process of the coated paper of FIG. 1 (Comparative Example 1) observed for 14 days, wherein the coated paper is pre-treated with UV for 6 hours before the biodegradation.
Figure 3:
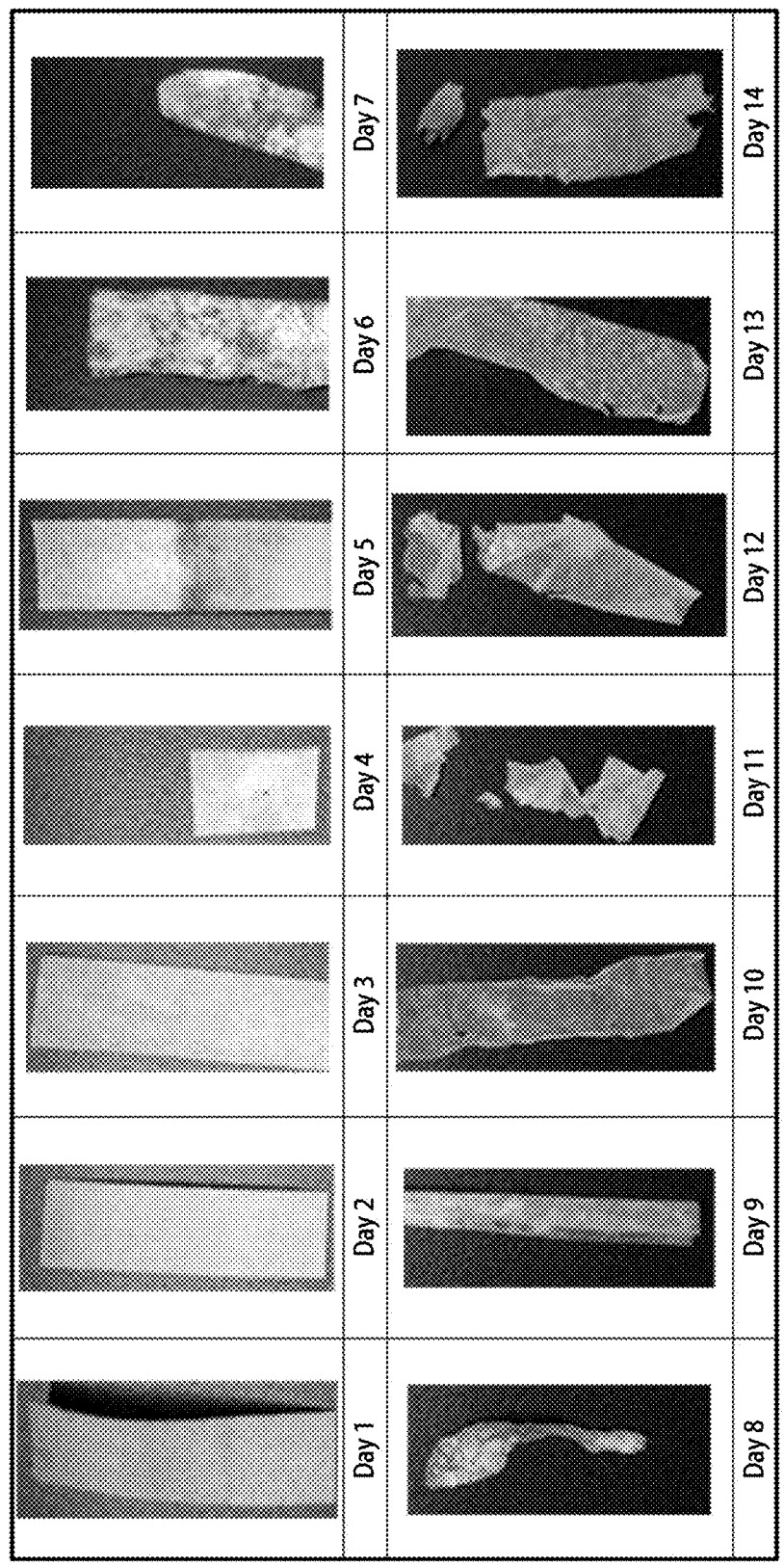
FIG. 3 is a photograph showing a biodegradation process of coated paper (Example 2) observed for 14 days, wherein the coated paper is manufactured according to a manufacturing method of the present invention.
Figure 4:
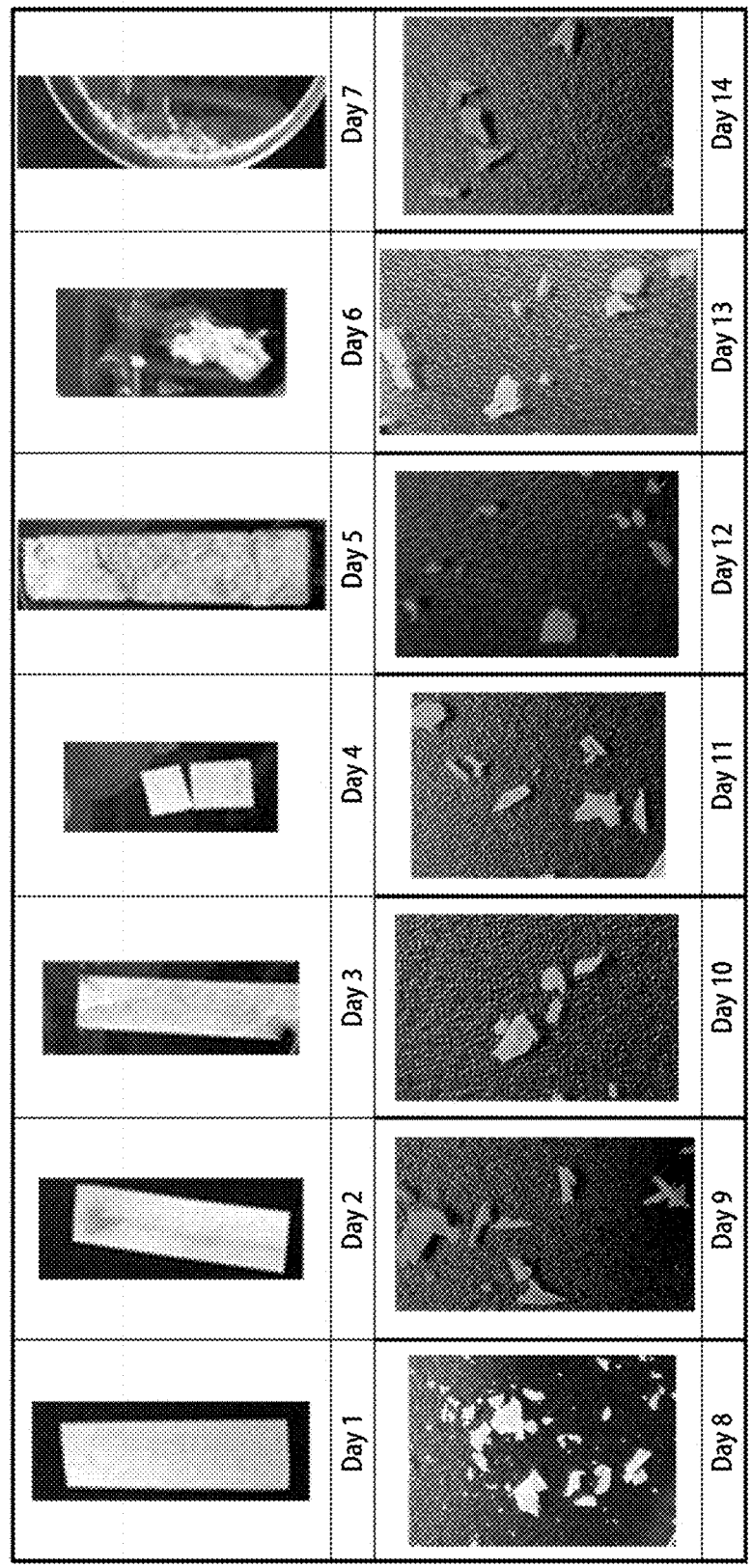
FIG. 4 is a photograph showing a biodegradation process of the coated paper of FIG. 3 (Example 2) overserved for 14 days, wherein the coated paper is pre-treated with UV for 6 hours before the biodegradation.

FIG. 1 is a photograph showing a biodegradation process of coated paper (Comparative Example 1) observed for 14 days, wherein the coated paper uses a conventional PE coating material according to a prior art, and FIG. 2 is a photograph showing a biodegradation process of the coated paper of FIG. 1 (Comparative Example 1) observed for 14 days, wherein the coated paper is pre-treated with UV for 6 hours before the biodegradation. FIG. 3 is a photograph showing a biodegradation process of coated paper (Example 2) observed for 14 days, wherein the coated paper is manufactured according to a manufacturing method of the present invention, and FIG. 4 is a photograph showing a biodegradation process of the coated paper of FIG. 3 (Example 2) overserved for 14 days, wherein the coated paper is pre-treated with UV for 6 hours before the biodegradation. In other words, the coated paper of FIG. 1 and FIG. 3 were not pre-treated with UV.

Referring to FIG. 1, in the case of Comparative Example 1 in which pre-treatment with UV was not performed, biodegradation by anaerobic microorganisms was carried out and no significant changes were observed until Day 3. However, it was confirmed that the anaerobic microorganisms were absorbed on the surface. From Day 5, the base paper used in the coated paper was swollen and fallen off and only the PE coating film remained. Thereafter, the biodegradation of the PE coating film was not observed by the naked eye.

Referring to FIG. 2, in the case of Comparative Example 1 in which the pre-treatment with UV was performed for 6 hours, no significant changes were observed until Day 5. From Day 6, a lot of the base paper fell off due to the swelling thereof caused by the anaerobic culture medium, and it was observed that only the PE coating film remained in the portion where the base paper was removed. From Day 7, only the PE coating film was present and thereafter, the biodegradation of the PE coating film was not observed with the naked eye.

Referring to FIG. 3, in the case of Example 2 in which the pre-treatment with UV was not performed, no significant changes were observed until Day 5. However, from Day 6, the base paper started to fall off from the film. From Day 9, it was observed that the base paper was removed by the anaerobic microorganisms and only the film remained. Thereafter, the coating film was observed in a torn shape.

Referring FIG. 4, in the case of Example 2 in which the pre-treatment with UV was performed for 6 hours, no significant changes were observed until Day 4. However, from Day 5, the biodegradation of the film started, and from Day 7, the coating film was observed to be almost broken due to biodegradation. Therefore, the oxidation of the coating film or the coating material of Example 2 was promoted due to UV irradiation, and in the case of the coating film of the present invention, it may be seen that the biodegradation thereof progresses well in a relatively short time.

Figure 5:
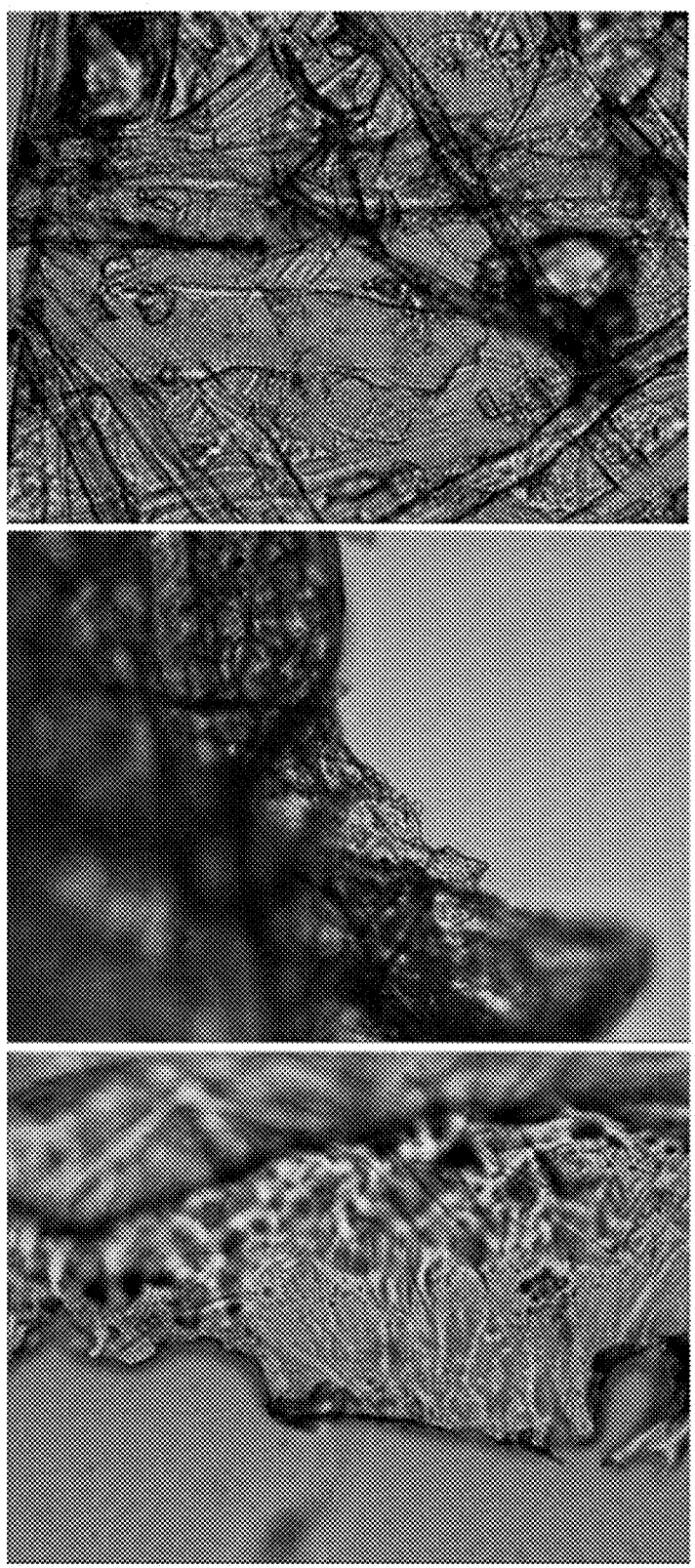
FIG. 5 is a photograph of the coating film of FIG. 4 observed with an optical microscope.

FIG. 5 is a photograph of the coating film of FIG. 4 observed with an optical microscope. Referring to FIG. 5, in the case of the coating film of Example 2, during the biodegradation experiment, it was observed that the bending and cracks occurred on the coating film. Since the anaerobic microorganisms infiltrate through such bending and cracks, the biodegradation reaction causes the coating film to be finely cut.

<2-6> Analysis of Structural Change of the Coated Paper by FT-IR

Figure 6A:
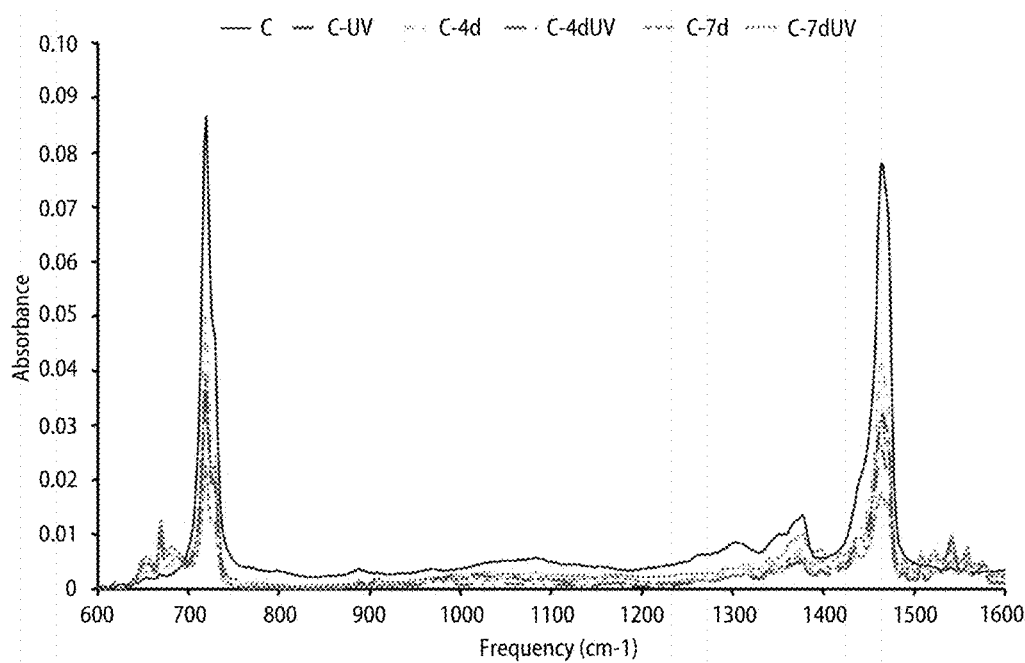
FIG. 6A is a graph showing FT-IR peaks measured in a range of 600-1600 $cm^{-1}$ for Comparative Example 1.
Figure 6B:
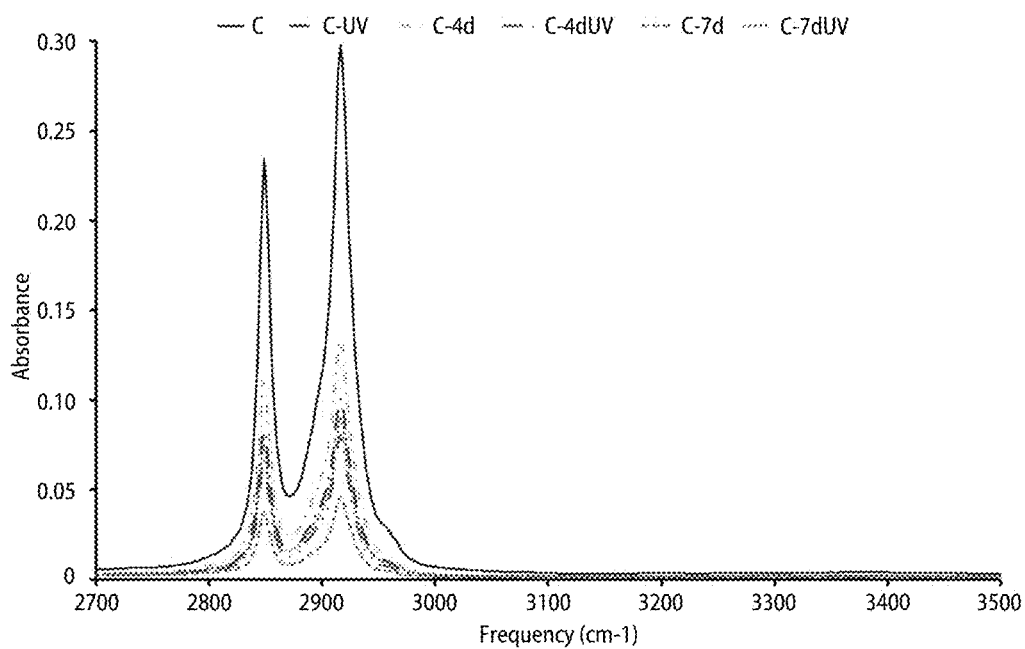
FIG. 6B is a graph showing FT-IR peaks measured in a range of 2700-3500 $cm^{-1}$ for Comparative Example 1.
Figure 7A:
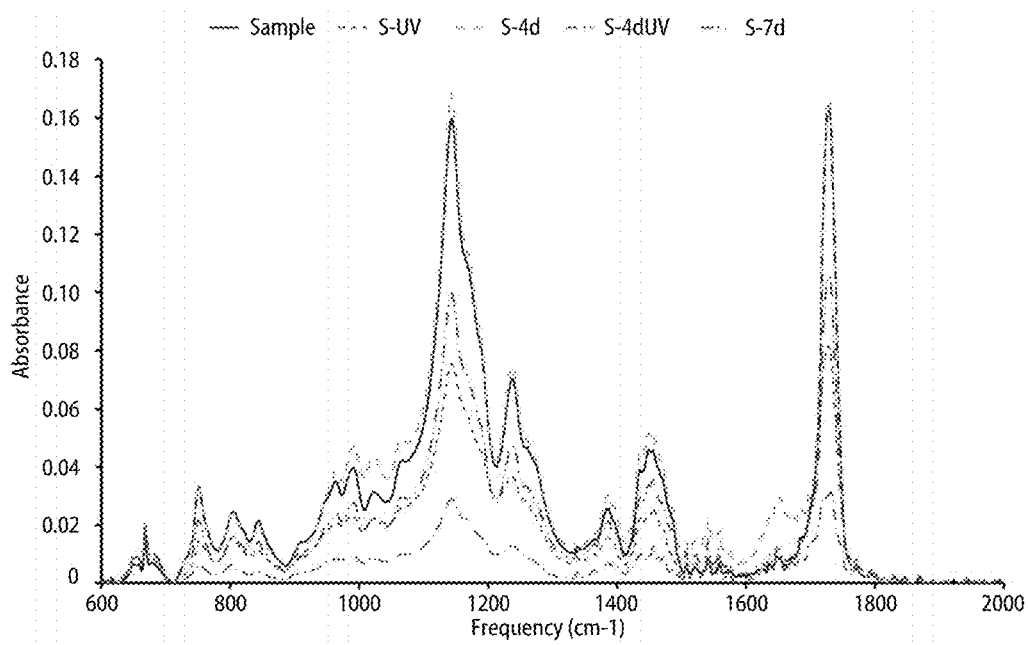
FIG. 7A is a graph showing FT-IR peaks measured in a range of 600-1600 $cm^{-1}$ for Example 2.
Figure 7B:
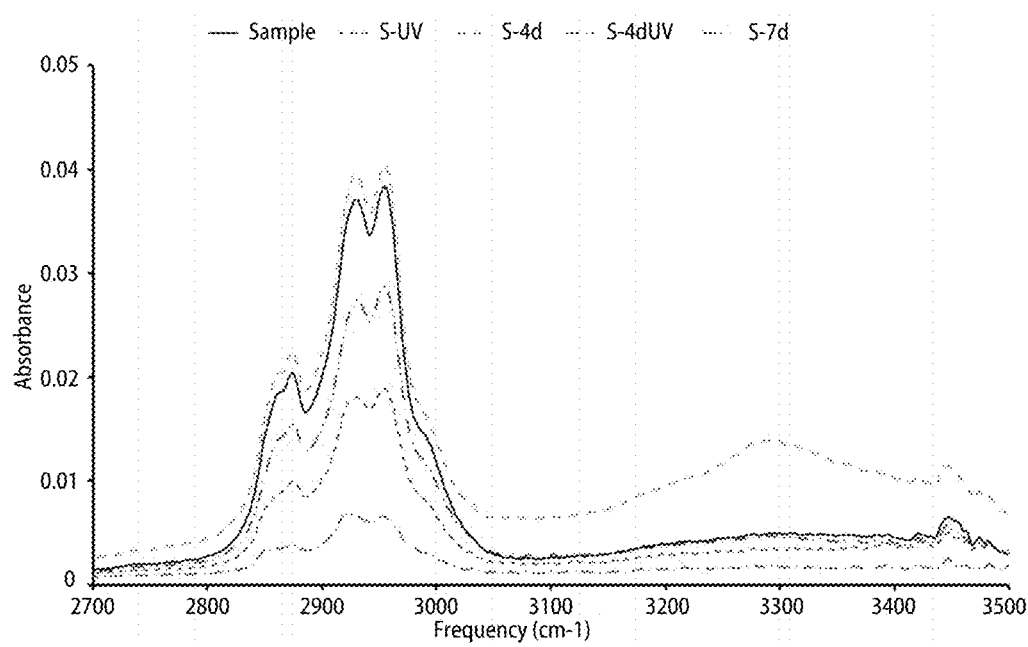
FIG. 7B is a graph showing FT-IR peaks measured in a range of 2700-3500 $cm^{-1}$ for Example 2.

FT-IR analysis was performed respectively on samples untreated for anaerobic microorganisms, samples treated for anaerobic microorganisms for 4 days, samples treated for anaerobic microorganisms for 7 days, and samples irradiated with UV. FIG. 6A is a graph showing FT-IR peaks measured in a range of 600-1600 $cm^{-1}$ for Comparative Example 1, and FIG. 6B is a graph showing FT-IR peaks measured in a range of 2700-3500 $cm^{-1}$ for Comparative Example 1. FIG. 7A is a graph showing FT-IR peaks measured in a range of 600-1600 $cm^{-1}$ for Example 2, and FIG. 7B is a graph showing FT-IR peaks measured in a range of 2700-3500 $cm^{-1}$ for Example 2.

Table 4 below summarizes the legend of FIGS. 6a to 7b.

TABLE 4

| With or Without UV treatment | Days of biodegradation treatment | Comparative Example 1 (FIG. 6a, FIG. 6b) | Example 2 (FIG. 7a, FIG. 7b) |
| --- | --- | --- | --- |
| Untreated with UV | 0 day | C | Sample |
| Untreated with UV | 4 days | C-4 d | S-4 d |
| Untreated with UV | 7 days | C-7 d | S-7 d |
| Treated with UV | 0 day | C-UV | S-UV |
| Treated with UV | 4 days | C-4 d UV | S-4 d UV |
| Treated with UV | 7 days | C-7 d UV |  |

FIGS. 6a and 6b show the analysis results of FT-IR for Comparative Example 1. —$CH_2$ group which is a characteristic peak of the PE coating film was observed at 2916 $cm^{-1}$ and 2848 $cm^{-1}$, and a peak corresponding to $CH_2$ deformation bending was observed at 1460 cm$^{-1}$. At 720 cm-$^1$, a peak corresponding to CH rocking bending was observed. These peaks showed a tendency to decrease slightly in proportion to the treatment period by UV treatment and anaerobic microbial treatment.

FIGS. 7a and 7b show the analysis results of FT-IR for Comparative Example 2. The coating film was almost biodegraded to such an extent that it was impossible to recover the coating film after 7 days from UV irradiation, thereby no analysis was performed. In the case of samples not treated with UV, no significant changes were observed until Day 4. However, all the peaks decreased on Day 7. In addition, in the case of samples irradiated with UV, it was observed on Day 4 that all the peaks showing the characteristics of the coating film of the present invention were greatly reduced and the UV treatment promoted biodegradation.

By such FT-IR analysis, it was observed that the coating film of Example 2 was generally more biodegradable than the PE film of Comparative Example 1.

Figure 8:
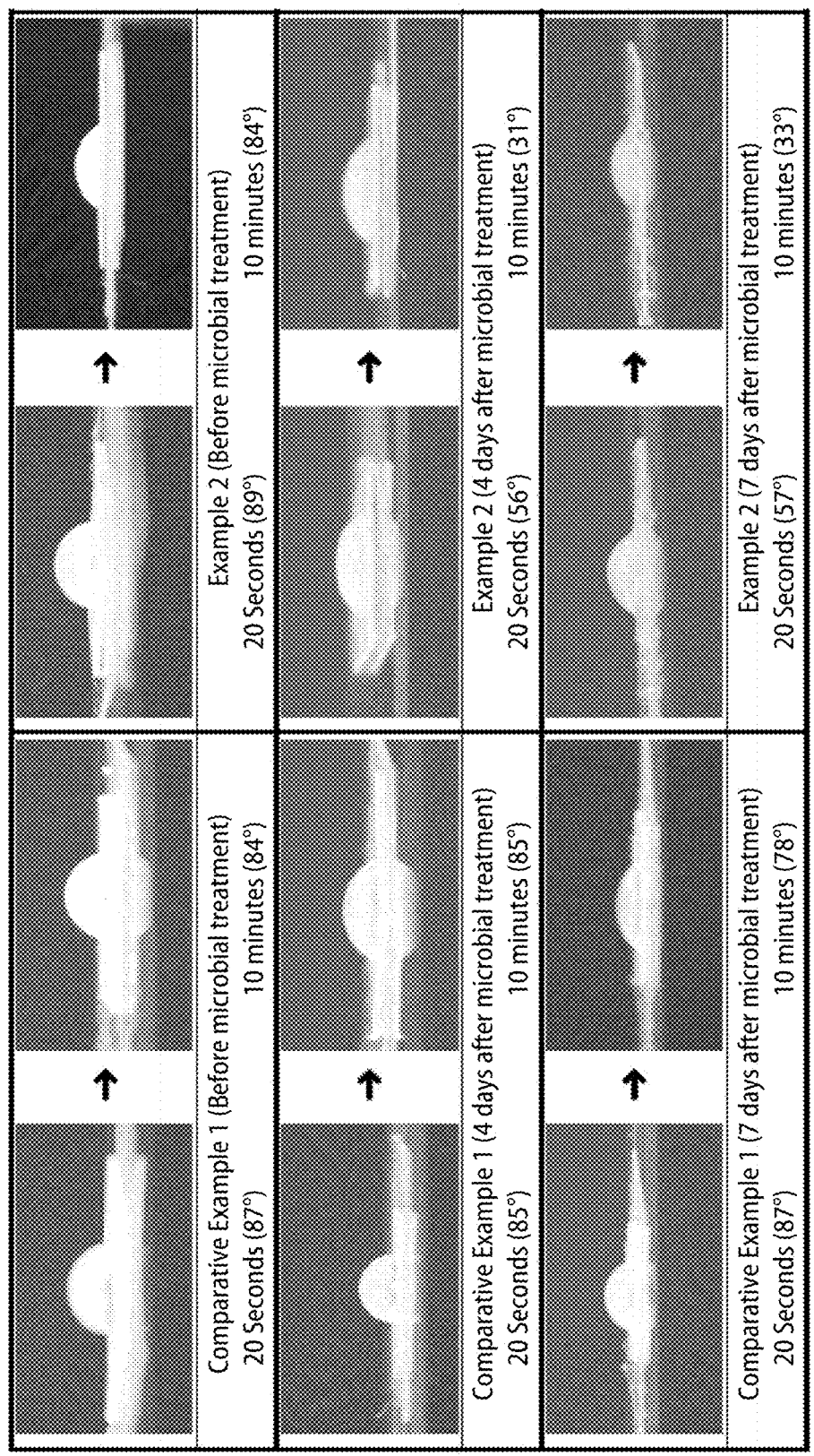
FIG. 8 is a photograph showing changes in a contact angle according to the treatment period of anaerobic microorganisms for samples not treated with UV (Example 2 and Comparative Example 1).

<2-7> Observation of the Contact Angle of Coated Paper Biodegraded by Anaerobic Microorganisms FIG. 8 is a photograph showing changes in a contact angle according to the treatment period of anaerobic microorganisms for samples not treated with UV (Example 2 and Comparative Example 1). In FIG. 8, the numbers in parentheses indicate the contact angles. In the case of the coated paper of Comparative Example 1, there was almost no change in the contact angle according to the treatment period (before the treatment, 4 days, and 7 days) of the anaerobic microorganisms. Also, the contact angle did not change significantly as the contact time of distilled water (20 seconds to 10 minutes elapsed) was increased. On the other hand, in the case of the coated paper of Example 2, on the 4th day of anaerobic microbial treatment, the contact angle of the sample decreased significantly compared to before treatment. Also, the contact angle according to the contact time (20 seconds to 10 minutes elapsed) decreased significantly compared to the sample before the anaerobic microbial treatment.

Figure 9:
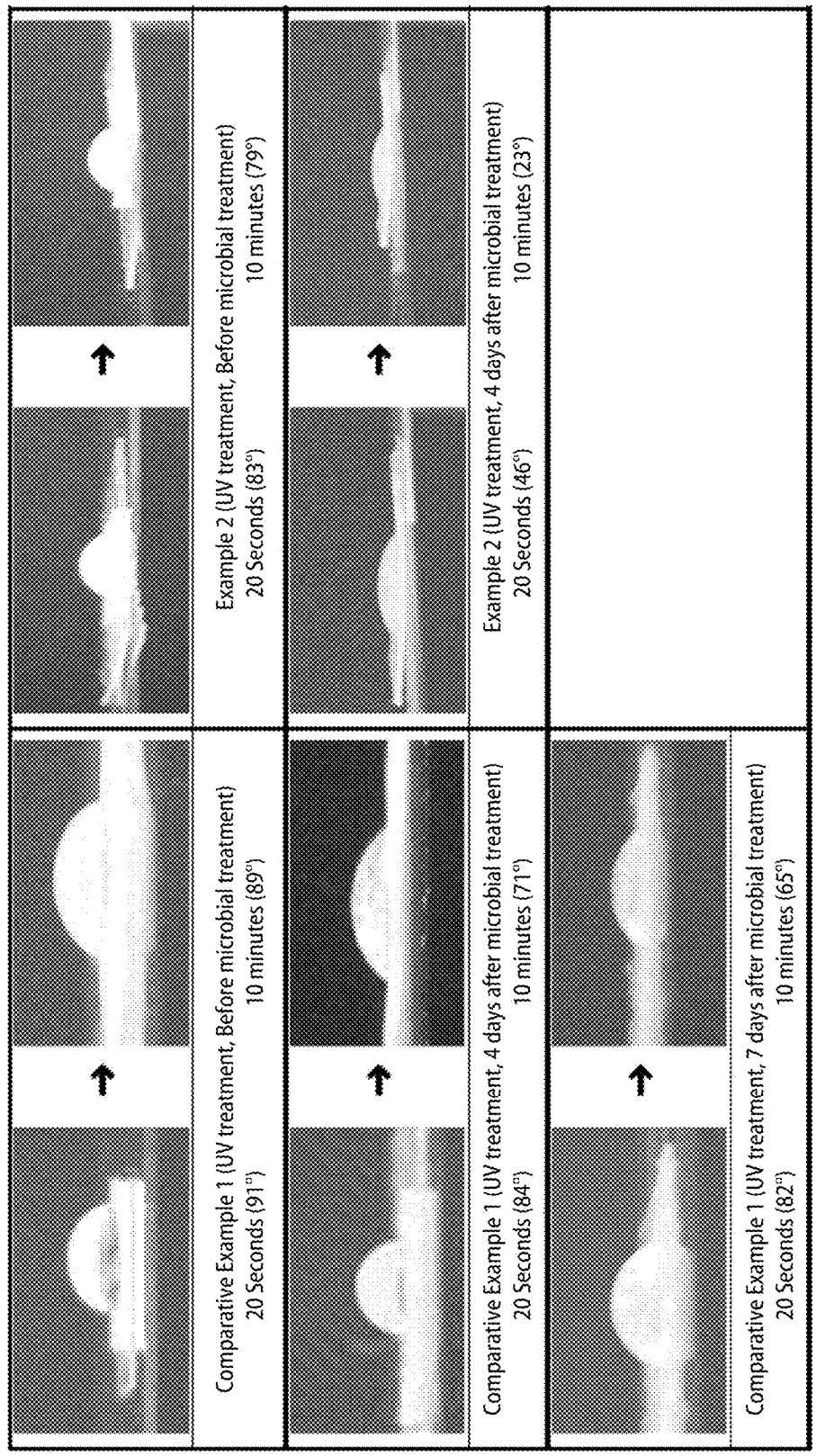
FIG. 9 is a photograph showing changes in a contact angle according to the treatment period of the anaerobic microorganisms for samples treated with UV (Example 2 and Comparative Example 1).

FIG. 9 is a photograph showing changes in a contact angle according to the treatment period of the anaerobic microorganisms for samples treated with UV (Example 2 and Comparative Example 1). In the case of the coated paper of Comparative Example 1, the contact angle after the first 20 seconds was slightly decreased as the anaerobic microbial treatment period was increased, and the contact angle did not change with increasing contact time. On the other hand, in the case of the coated paper of Example 2, the contact angle was greatly decreased in the samples on the 4th day after anaerobic microbial treatment, and the contact angle was greatly decreased as the contact time increased.

Therefore, it was observed that the coated paper according to Example 2 of the present invention had better biodegradability by anaerobic microbial treatment than the PE coated paper of Comparative Example 1.

Experimental Example 3

Test for Recyclability

<3-1> Preparation of Samples

The recyclability of the coated paper (Comparative Example 1) coated with polyethylene (PE), the coated paper (Comparative Example 2) coated with polylactic acid (PLA), and the coated paper (Example 2) prepared according to the manufacturing method of the present invention was compared and analyzed.

<3-2> Equipment for the Experiment

A. Pilot Pulper

A low density pulper (Lamort Lam'deinkit, France) was used to dissociate the coated paper samples. The rotor in the lower part of the pulper rotates to dissociate the disposable paper cup sample. The pulper vat is made of stainless steel, and baffles are installed therein to facilitate the flow of the paper material during dissociation.

B. Pilot Screen

Screen is a main unit process that may evaluate the dissociation property of coated paper as a process of classifying the constituents of paper material according to their size. The screen used in this experiment has both holes and slots such that the samples may be carefully sorted according to the size of foreign matter in stages. When the sample flows into the screen by the driving force of the pump, the sample moves to the inside of the screen through the hole of 3 mm in diameter under the screen. At this time, a material larger than the diameter of the hole may not pass through the hole and is discharged through a reject. The sample introduced into the screen passes through a slot of 0.3 mm in size due to the centripetal force generated by the rotating force of foil, and the material that did not pass through the slot is classified through a slot reject valve.

C. Somerville Screen and Flotation Cell

The Somerville screen is a device equipped with a slot of 0.15 mm in size and is used to classify flakes and fibers. The flotation cell is equipment by which hydrophobic particles (ink, ash, etc.) dispersed in the paper material are attached to the surface of a bubble by a physicochemical method, floated, removed and classified. Components classified by the flotation were quantitatively analyzed using the equipment.

<3-3> Method for the Experiment

Figure 10:
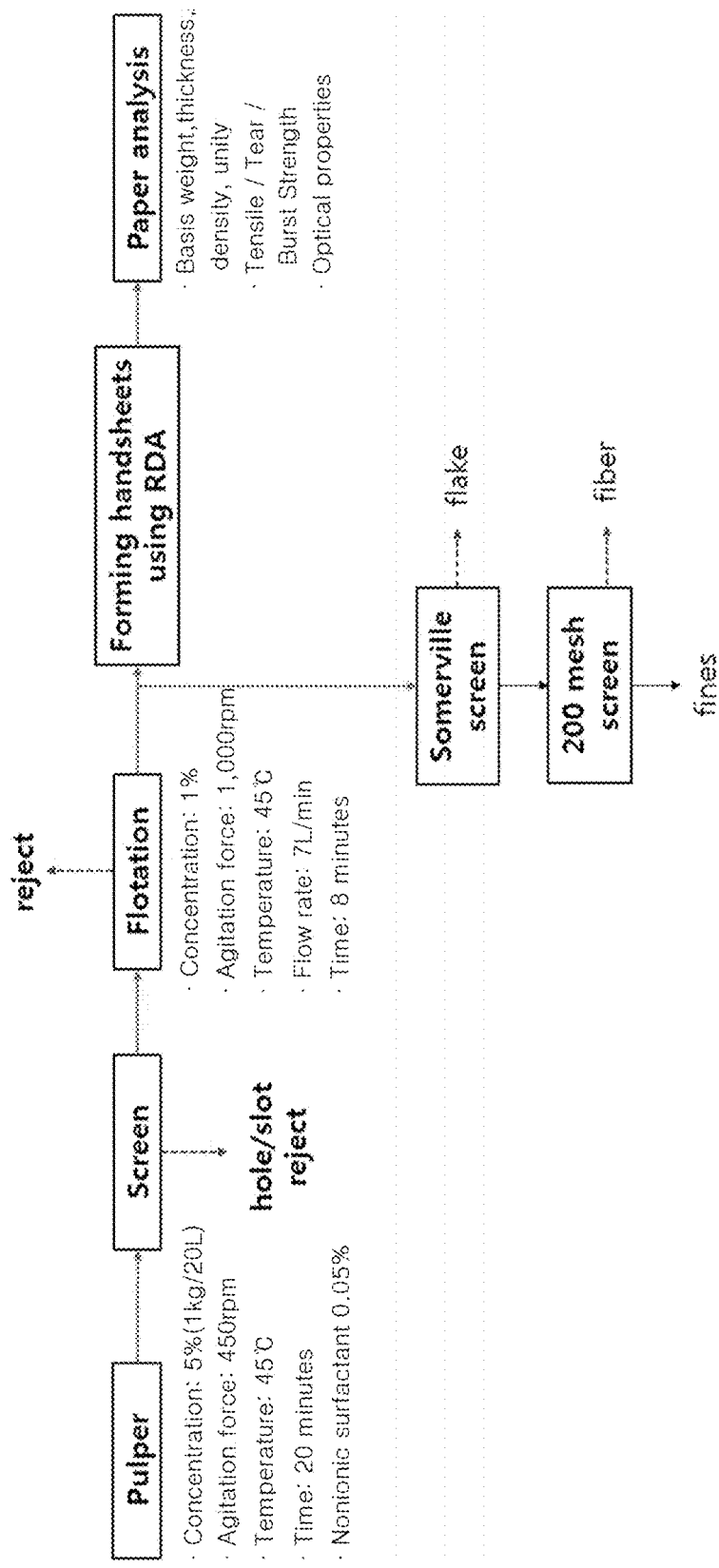
FIG. 10 illustrates a procedure of analysis experiment on the recyclability of coated paper of the present invention.

FIG. 10 illustrates a procedure of analysis experiment on the recyclability of coated paper of the present invention. Referring to FIG. 10, first, 20 L of water which was adjusted to have a calcium hardness of 300 ppm and a temperature of 45° C., and 1 kg of coated paper were added to the pilot pulper, and the concentration was adjusted to 5 wt %. 0.05 wt % of non-ionic surfactant based on the weight of the coated paper was added thereto, thereafter, the mixture was stirred at a rotation speed of 450 rpm for 20 minutes, and holes and slot rejections were respectively classified after the pilot screen. The controllability of flakes was investigated by processing the screen accept by flotation. After controlling the screen accept to have a concentration of 1 wt %, and a temperature of 45° C. and stirring the controlled screen accept at 1000 rpm, air was injected at a flow rate of 7 L/min to process the material by flotation. After the flotation, the contents of flakes, fibers, fines of the flotation acceptance were quantitatively analyzed by the Somerville screen. By using the fibers obtained from the Somerville screen, a weeping paper was made and the strength and optical properties thereof were analyzed.

<3-4> Analysis Results of Rejection and Yield

Figure 11:
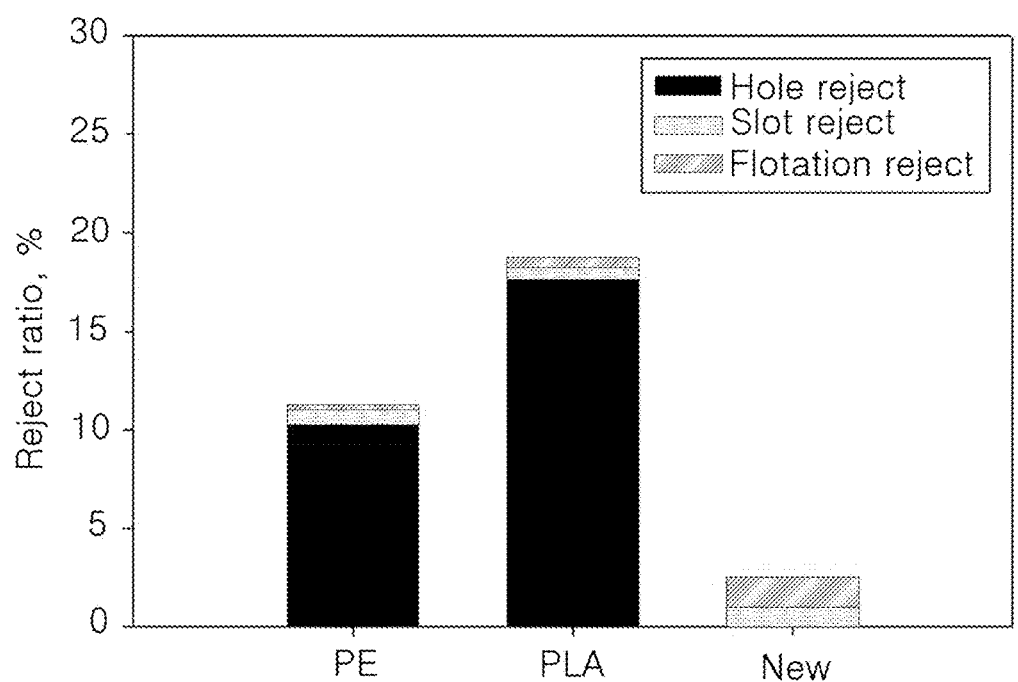
FIG. 11 shows the analysis results for hole/slot rejection and floatation rejection of a pilot screen generated during the recyclability analysis experiment process of FIG. 10.

FIG. 11 shows the analysis results for hole/slot rejection and floatation rejection of a pilot screen generated during the recyclability analysis experiment process of FIG. 10. As shown in FIG. 11, the hole rejection classified after the pilot screen was analyzed to be 10.26% for the coated paper (PE) of Comparative Example 1, and 17.63% for the coated paper (PLA) of Comparative Example 2. The hole rejection of the coated paper (New) of Example 2 did not occur. The slot rejection was less than 1% in all coated paper. In the case of rejection classified after the flotation was 0.21% for the coated paper (PE) of Comparative Example 1, 0.42% for the coated paper (PLA) of Comparative Example 2, and 1.52% for the coated paper (New) of Example 2. In Example 2, the reason for the relatively large number of flotation rejects is that the letters, pictures, and the like printed on the coated paper of Example 2 were combined with the coating film to become flakes and then classified as floating rejects.

Overall, Example 2 of the present invention showed a significantly lower rejection ratio than Comparative Example 1 and Comparative Example 2. That is, the coated paper of Example 2 has high recyclability because there were very few film-type foreign substances that could not pass through the screen of the waste paper recycling process

EXPERIMENTAL EXAMPLE 4

Test for Heat-resistant Property

Figure 12:
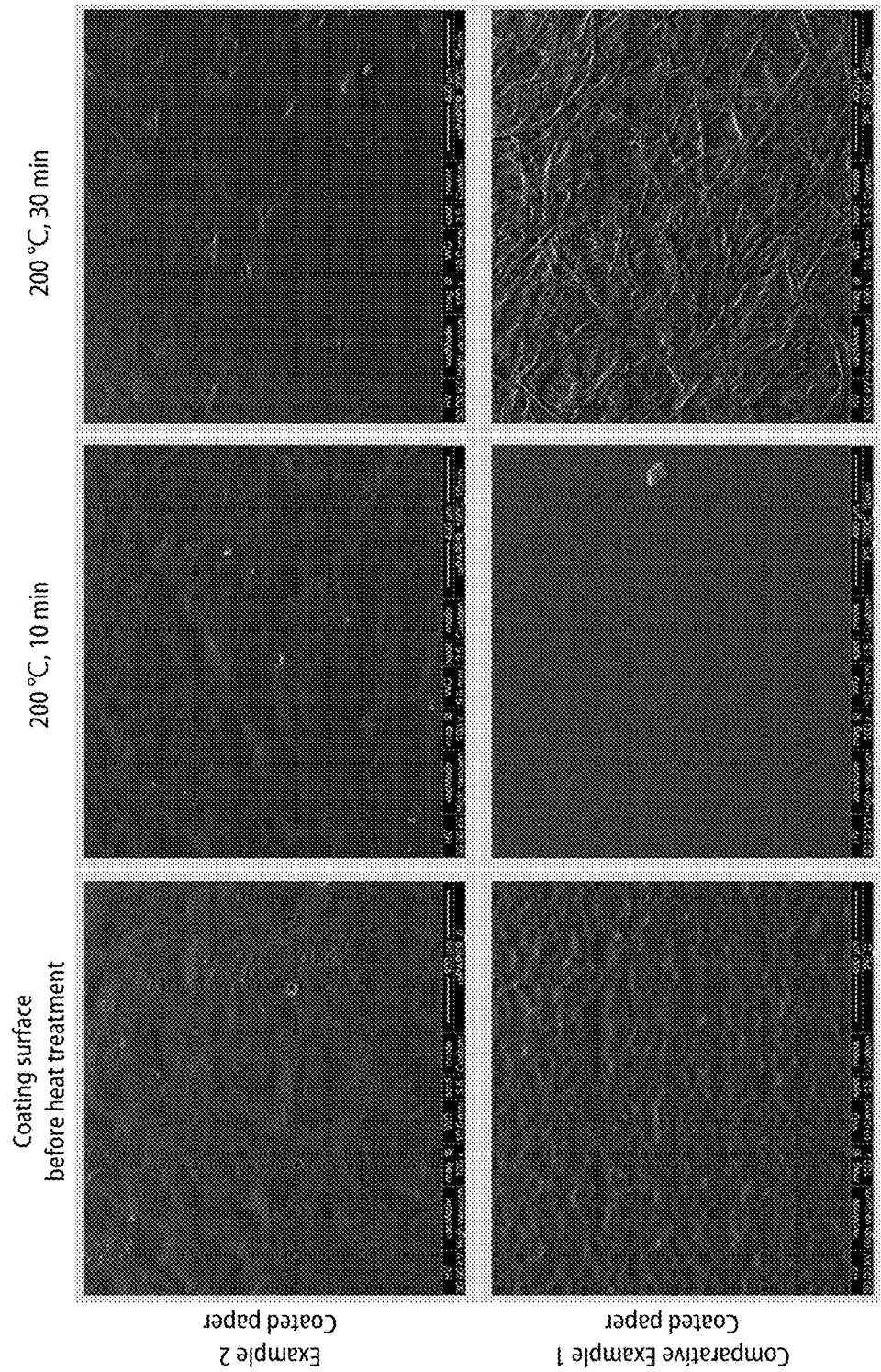
FIG. 12 is an SEM photograph showing the surface of a coating layer before and after the coated paper of Example 2 and Comparative Example 1 is heat-treated.
Figure 13:
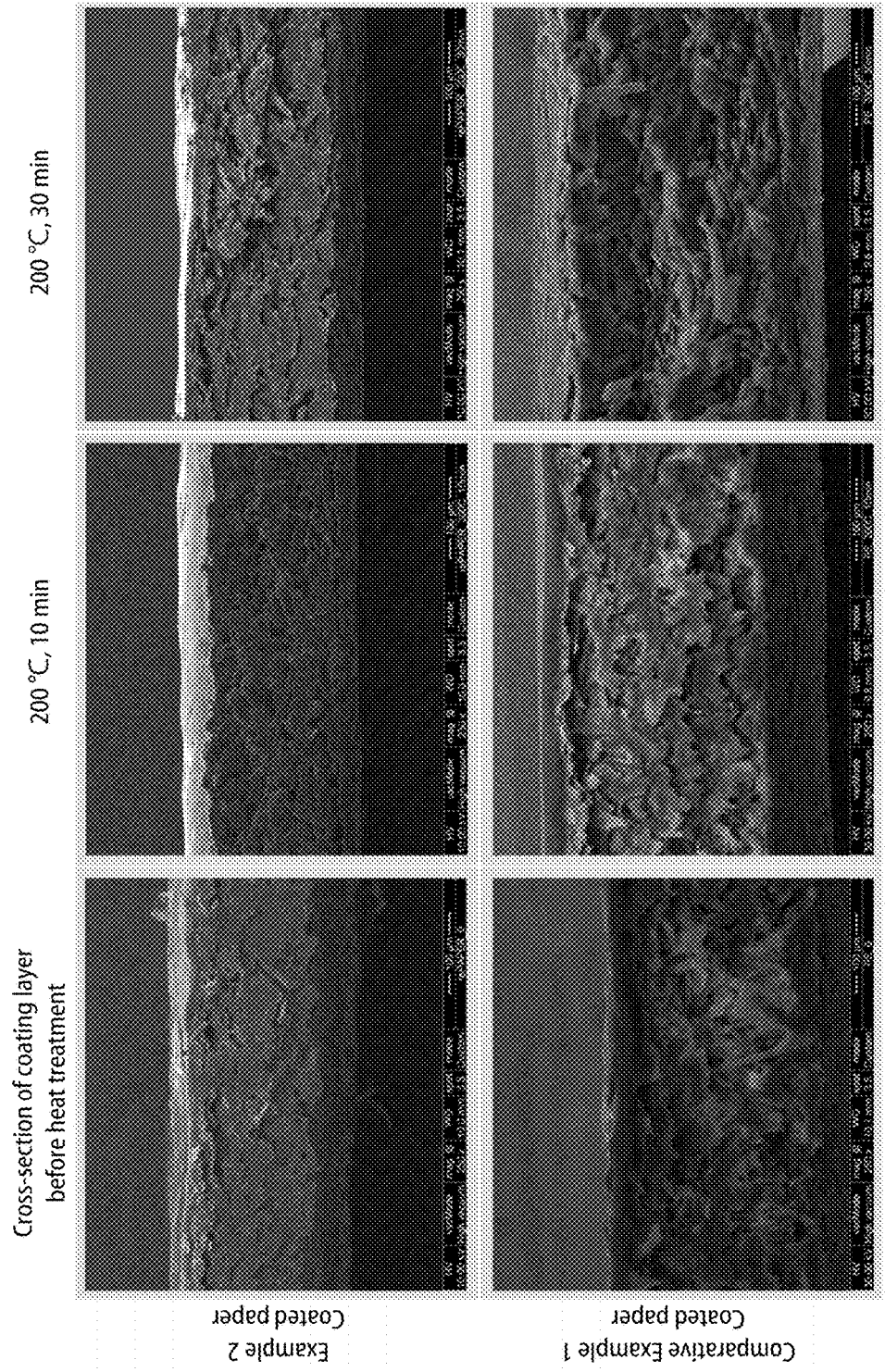
FIG. 13 is a SEM photograph showing the cross section of the coating layer before and after the coated paper of Example 2 and Comparative Example 1 is heat-treated.

In order to test the heat resistant property of the coating layers of Example 2 and Comparative Example 1, the coated paper of each sample was heat-treated at 200° C. for 10 minutes and for 30 minutes, and then the coating layer thereof was observed with a scanning electron microscope (SEM). FIG. 12 is an SEM photograph showing the surface of a coating layer before and after the coated paper of Example 2 and Comparative Example 1. FIG. 13 is a SEM photograph showing the cross section of the coating layer before and after the coated paper of Example 2 and Comparative Example 1.

Referring to FIG. 12, the coating layer of Example 2 hardly changed before or after the heat treatment (200° C. for 10 minutes or 200° C. for 30 minutes). Therefore, the coated paper of the present invention may be suitably used as a heat-resistant food container. On the other hand, in the case of the coating layer of Comparative Example 1 using the PE coating material, when the heat treatment was performed at 200° C. for 10 minutes, the coating layer was instantly melted to show a clean surface and when the heat treatment was performed for 30 minutes, the fibrosis of polyethylene occurred, thereby causing the deformation of the coating layer.

Referring to FIG. 13, the coating layer of Example 2 still remained on the base paper for cups after the heat treatment and still functioned as a coating layer. However, when the coating layer of Comparative Example 1 was heat-treated at 200° C. for 30 minutes, most of the coating layer was melted and permeated into the inside of the base paper for cups and therefore, the function as the coating layer was lost.

EXPERIMENTAL EXAMPLE 5

Test for Food Stability (FDA Certified)

FIG. 14 shows the results of experiment obtained by requesting a US certification company (UL Verification Services, Inc.) to perform the experiment on the coated paper of the present invention. This experiment was conducted on food stability at room temperature and indicates compliance with the requirements of FDA 21 CFR 175.300. The coated paper of the present invention has passed the above FDA 21 CFR 175.300 test and is recognized as suitable for food and beverage handling applications.

Furthermore, FIG. 15 shows the results of experiment obtained by requesting a global certification company (SGS) to perform the experiment on the coated paper of the present invention. This experiment was conducted to measure the amount of chloroform coming from the coated paper at a high temperature (250° F.≈121° C., 150° F.≈66° C.) and no chloroform was detected in the coated paper of the present invention. It has been recognized that the coated paper of the present invention passed the US FDA 21 CFR 176.170 test.

EXPERIMENTAL EXAMPLE 6

Test for Environmental Hormone Stability

FIG. 16 is a graph showing the results of experiment regarding whether to detect phthalate, an environmental hormone, by requesting a global certification company (SGS) to perform the experiment on the coated paper of the present invention.

Although the paper coating material of the present invention includes a copolymer emulsion in which the silicon-based polymer and the acryl-based polymer are copolymerized, and a colloidal aqueous solution of gelatinized polyvinyl alcohol mixed therewith, the present invention is not limited to this example. The paper coating material may be a copolymer emulsion in which the colloidal aqueous solution of polyvinyl alcohol is excluded. Here, the weight ratio of the acryl-based polymer and the silicon-based polymer is preferably 99:1 to 99.9:0.1.

Hereinafter, preferred embodiments of the present invention will be described in detail with reference to the accompanying drawings. It is to be understood, however, that these examples are offered by way of illustration only, and the scope of the present invention is not limited to these examples.

What is claimed is:
1. A method of manufacturing a paper coating material, the method comprising:
   (a) adding, to a reactor, water, acryl-based monomer, an initiator, an emulsifier, and a buffer;
   (b) adding a silicon-based monomer to the reactor at a uniform rate;
   (c) producing a copolymer emulsion having a weight average molecular weight of 100,000 to 200,000 by adjusting the temperature of the reactor;
   (d) putting water and polyvinyl alcohol into a separate container and stir prepare a colloidal aqueous solution of gelatinized polyvinyl alcohol; and
   (e) adding the colloidal aqueous solution of gelatinized polyvinyl alcohol to the copolymer emulsion.

2. The method of claim 1, wherein the weight ratio between an acryl-based monomer and a silicon-based monomer, which form the copolymer emulsion, is 99:1 to 99.9:0.1.

3. The method of claim 2, wherein the weight ratio between the copolymer emulsion and the colloidal aqueous solution of polyvinyl alcohol is 85:15 to 95:5 based on a solid content.

4. The method of claim 1, wherein the colloidal aqueous solution of gelatinized polyvinyl alcohol is prepared by adding 7 to 15 wt % of polyvinyl alcohol into water and stirring for 1 to 10 minutes at a temperature of 85 to 98° C.

5. The method of claim 1, wherein the glass transition temperature of the copolymer component of the copolymer emulsion is 300 to 340° C.

6. The method of claim 1, wherein the degree of saponification of the polyvinyl alcohol is 92 to 99 mol %.

7. The method of claim 1, wherein in step (a), the temperature of the reactor is maintained at 50 to 70° C., and in step (c), the temperature of the reactor is maintained at 70 to 90 ° C.

8. A paper coating material comprising:

a copolymer emulsion in which a silicon-based polymer having a repeating unit represented by formula 1 below and an acryl-based polymer having a repeating unit represented by formula 2 below are copolymerized, wherein particles included in the copolymer emulsion have a weight average molecular weight of 100,000 to 200,000; and a colloidal aqueous solution of gelatinized polyvinyl alcohol mixed with the copolymer emulsion,

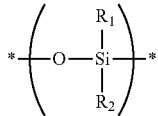
[Formula 1]

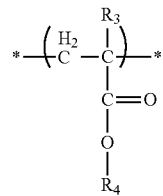
[Formula 2]

in formulae 1 and 2 above, R1 to R4 may be same or different, and are each independently hydrogen, or a substituted or unsubstituted alkyl group or aryl group.

9. The paper coating material of claim 8, wherein the weight ratio between the acryl-based polymer and the silicon-based polymer is 99:1 to 99.9:0.1.

10. The paper coating material of claim 9, wherein the weight ratio of the copolymer emulsion and the colloidal aqueous solution of polyvinyl alcohol is 85:15 to 95:5 based on a solid content.

11. The method of claim 1, wherein the glass transition temperature of the copolymer component of the copolymer emulsion is 300 to 340° C.

12. The paper coating material of claim 8, wherein the degree of saponification of the polyvinyl alcohol is 92 to 99 mol %.

* * * * *